US012758331B2

(12) United States Patent
Thompson et al.

(10) Patent No.: US 12,758,331 B2
(45) **Date of Patent: *Oct. 13, 2026**

(54) TELESCOPING CANNULA ARM

(71) Applicant: INTUITIVE SURGICAL OPERATIONS, INC., Sunnyvale, CA (US)

(72) Inventors: Allen C. Thompson, Los Altos, CA (US); Daniel H. Gomez, Los Gatos, CA (US); Kirk Nangreaves, Campbell, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 168 days.

This patent is subject to a terminal disclaimer.

(21) Appl. No.: 18/595,803

(22) Filed: Mar. 5, 2024

(65) Prior Publication Data

US 2024/0277428 A1 Aug. 22, 2024

Related U.S. Application Data

(63) Continuation of application No. 17/718,201, filed on Apr. 11, 2022, now Pat. No. 11,950,866, which is a (Continued)

(51) Int. Cl.
*A61B 34/30* (2016.01)
*A61B 34/00* (2016.01)

(Continued)

(52) U.S. Cl.
CPC .............. *A61B 34/30* (2016.02); *A61B 34/70* (2016.02); *A61B 46/10* (2016.02); *A61B 90/50* (2016.02);

(Continued)

(58) Field of Classification Search
CPC ......... A61B 34/30; A61B 34/70; A61B 34/72; A61B 2034/301-305; A61B 90/50; A61B 2090/508
See application file for complete search history.

(56) References Cited

U.S. PATENT DOCUMENTS 5,584,818 A 12/1996 Morrison
5,599,318 A 2/1997 Sweeney et al.

(Continued)

FOREIGN PATENT DOCUMENTS

CN 1636607 A 7/2005
CN 201244076 Y 5/2009

(Continued)

OTHER PUBLICATIONS

Extended European Search Report for Application No. EP25187356.8 mailed on Sep. 15, 2025, 7 pages.

(Continued)

*Primary Examiner* — Todd J Scherbel
(74) *Attorney, Agent, or Firm* — Artegis Law Group, LLP

(57) ABSTRACT

A system includes a manipulator arm and a cannula mount arm. The manipulator arm includes a link and a locking assembly coupled to the link. The cannula mount arm includes a latch. The cannula mount arm is configured to be extended from the link to an extended position. The locking assembly is configured to engage with the latch when the cannula mount arm is extended from the link to the extended position so as to lock the cannula mount arm in the extended position. Activation of an electrical component coupled to the locking assembly is inhibited when a cannula is docked to the cannula mount arm.

20 Claims, 14 Drawing Sheets

Related U.S. Application Data continuation of application No. 15/774,240, filed as application No. PCT/US2016/067694 on Dec. 20, 2016, now Pat. No. 11,331,154.

(60) Provisional application No. 62/276,136, filed on Jan. 7, 2016.

(51) Int. Cl.

| | |
|---|---|
| ***A61B 46/10*** | (2016.01) |
| ***A61B 90/50*** | (2016.01) |
| *A61B 17/00* | (2006.01) |
| *A61B 17/34* | (2006.01) |

(52) U.S. Cl.

CPC . *A61B 2017/00991* (2013.01); *A61B 17/3421* (2013.01)

(56) References Cited

U.S. PATENT DOCUMENTS

| | | | | |
|---|---|---|---|---|
| 5,957,933 | A | 9/1999 | Yanof et al. | |
| 6,671,581 | B2 | 12/2003 | Niemeyer et al. | |
| 9,060,678 | B2 | 6/2015 | Larkin et al. | |
| 9,408,526 | B2 | 8/2016 | Gale et al. | |
| 10,456,208 | B2 | 10/2019 | Thompson et al. | |
| 11,331,154 | B2 | 5/2022 | Thompson et al. | |
| 11,950,866 | B2 * | 4/2024 | Thompson | A61B 34/70 |
| 2004/0199140 | A1 | 10/2004 | Rue et al. | |
| 2006/0241655 | A1 | 10/2006 | Viola | |
| 2007/0010843 | A1 | 1/2007 | Green | |
| 2008/0140087 | A1 | 6/2008 | Barbagli | |
| 2009/0269179 | A1 | 10/2009 | Gale et al. | |
| 2010/0168762 | A1 | 7/2010 | Osawa et al. | |
| 2011/0277775 | A1 | 11/2011 | Holop et al. | |
| 2011/0277776 | A1 | 11/2011 | McGrogan et al. | |
| 2012/0024091 | A1 | 2/2012 | Kawabuchi et al. | |
| 2013/0204271 | A1 | 8/2013 | Brisson et al. | |
| 2015/0020916 | A1 | 1/2015 | Menon et al. | |
| 2017/0128120 | A1 | 5/2017 | Cho et al. | |
| 2022/0233259 | A1 | 7/2022 | Thompson et al. | |

FOREIGN PATENT DOCUMENTS

| | | | |
|---|---|---|---|
| CN | 101530347 | A | 9/2009 |
| CN | 101790822 | A | 7/2010 |
| CN | 201578363 | U | 9/2010 |
| CN | 101919739 | A | 12/2010 |
| CN | 102038998 | A | 5/2011 |
| CN | 102257292 | A | 11/2011 |
| CN | 103687559 | A | 3/2014 |
| CN | 104188710 | A | 12/2014 |
| CN | 104929437 | A | 9/2015 |
| CN | 104970864 | A | 10/2015 |
| CN | 204683756 | U | 10/2015 |
| DE | 19732212 | A1 | 1/1999 |
| DE | 69513345 | T2 | 3/2000 |
| EP | 1815949 | A1 | 8/2007 |
| EP | 2606838 | A1 | 6/2013 |
| JP | H0430403 | A | 2/1992 |
| JP | H0956046 | A | 2/1997 |
| JP | H11244281 | A | 9/1999 |
| JP | 2003527886 | A | 9/2003 |
| JP | 2006218563 | A | 8/2006 |
| KR | 20100085487 | A | 7/2010 |
| WO | WO-0033726 | A1 | 6/2000 |
| WO | WO-2010151510 | A1 | 12/2010 |
| WO | WO-2011037718 | A1 | 3/2011 |
| WO | WO-2011060042 | A1 | 5/2011 |
| WO | WO-2011143016 | A1 | 11/2011 |
| WO | WO-2014021222 | A1 | 2/2014 |
| WO | WO-2015023730 | A1 | 2/2015 |
| WO | WO-2015142814 | A1 | 9/2015 |

OTHER PUBLICATIONS

Extended European Search Report for Application No. 16884185.6 mailed on Jul. 17, 2019, 7 pages.
Extended European Search Report for Application No. EP23192207.1, mailed on Nov. 3, 2023, 07 pages.
International Search Report and Written Opinion for Application No. PCT/US2016/067694, mailed on Apr. 10, 2017, 13 pages.
Office Action mailed Aug. 18, 2020 for Japanese Application No. 2018535006 filed Dec. 20, 2016, 15 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

TELESCOPING CANNULA ARM

RELATED APPLICATIONS

This application is a continuation of U.S. patent application Ser. No. 17/718,201, entitled "TELESCOPING CANNULA ARM" and filed Apr. 11, 2022, which is a is a continuation of U.S. patent application Ser. No. 15/774,240, entitled "TELESCOPING CANNULA ARM" and filed May 7, 2018, which is a U.S. National Stage application of International Patent Application No. PCT/US2016/067694 filed on Dec. 20, 2016, the benefit of which is claimed and claims priority to and the benefit of the filing date of U.S. Provisional Patent Application 62/276,136, entitled "TELESCOPING CANNULA ARM" and filed Jan. 7, 2016, each of which is incorporated by reference herein in its entirety.

BACKGROUND

Field of the Invention

The present invention relates generally to cannula arms for computer-assisted surgical system, and more particularly to a telescoping cannula arm for the computer-assisted surgical system.

Description of Related Art

A sterile surgical drape has been previously used to cover a surgical manipulator and a plurality of instrument manipulators 140 in computer-assisted surgical system 100. The drapes have taken various forms. In each instance, the manipulator and associated supports links are covered with a sterile surgical drape prior to the start of a surgical procedure.

Surgical system 100 is a computer assisted surgical system that includes an endoscopic imaging system 192, a surgeon's console 194 (master), and a patient side support system 110 (slave), all interconnected by wired (electrical or optical) or wireless connections 196. One or more electronic data processors may be variously located in these main components to provide system functionality. Examples are disclosed in U.S. patent application Ser. No. 11/762,165, which issued as U.S. Pat. No. 9,060,678 and is incorporated by reference herein. Arrow 190 shows the distal and proximal directions used in the discussion of FIG. 1.

Imaging system 192 performs image processing functions on, e.g., captured endoscopic imaging data of the surgical site and/or preoperative or real time image data from other imaging systems external to the patient. Imaging system 192 outputs processed image data (e.g., images of the surgical site, as well as relevant control and patient information) to a surgeon at surgeon's console 194. In some aspects, the processed image data is output to an optional external monitor visible to other operating room personnel or to one or more locations remote from the operating room (e.g., a surgeon at another location may monitor the video; live feed video may be used for training; etc.).

Surgeon's console 194 includes multiple degrees-of-freedom ("DOF") mechanical input devices ("masters") that allow the surgeon to manipulate the instruments, entry guide(s), and imaging system devices, which are collectively referred to as slaves. These input devices may in some aspects provide haptic feedback from the instruments and surgical device assembly components to the surgeon. Console 194 also includes a stereoscopic video output display positioned such that images on the display are generally focused at a distance that corresponds to the surgeon's hands working behind/below the display screen. These aspects are discussed more fully in U.S. Pat. No. 6,671,581, which is incorporated by reference herein.

Control during insertion of the instruments may be accomplished, for example, by the surgeon moving the instruments presented in the image with one or both of the masters; the surgeon uses the masters to move the instrument in the image side to side and to pull the instrument towards the surgeon. The motion of the masters commands the imaging system and an associated surgical device assembly to steer towards a fixed center point on the output display and to advance inside the patient.

In one aspect, the camera control is designed to give the impression that the masters are fixed to the image so that the image moves in the same direction that the master handles are moved. This design causes the masters to be in the correct location to control the instruments when the surgeon exits from camera control, and consequently this design avoids the need to clutch (disengage), move, and declutch (engage) the masters back into position prior to beginning or resuming instrument control.

Base 101 of patient side support system 110 supports an arm assembly that includes a passive, uncontrolled setup arm assembly 120 and an actively controlled manipulator arm assembly 130. Actively controlled manipulator arm assembly 130 is sometimes referred to as entry guide manipulator 130.

In one example, the setup portion includes a first setup link 102 and two passive rotational setup joints 103 and 105. Rotational setup joints 103 and 105 allow manual positioning of the coupled setup links 104 and 106 if the joint brakes for setup joints 103 and 105 are released. Alternatively, some of these setup joints may be actively controlled, and more or fewer setup joints may be used in various configurations. Setup joints 103 and 105 and setup links 104 and 106 allow a person to place entry guide manipulator 130 at various positions and orientations in Cartesian x, y, z space. A passive prismatic setup joint (not shown) between link 102 of arm assembly 120 and base 101 may be used for large vertical adjustments 112.

A remote center of motion 146 is a location at which yaw, pitch, and roll axes intersect (i.e., the location at which the kinematic chain remains effectively stationary while joints move through their range of motion). Some of these actively controlled joints are manipulators that are associated with controlling DOFs of individual instruments, and others of these actively controlled joints are associated with controlling DOFs of a single assembly of these manipulators. The active joints and links are movable by motors or other actuators and receive movement control signals that are associated with master arm movements at surgeon's console 194.

As shown in FIG. 1, a manipulator assembly yaw joint 111 is coupled between an end of setup link 106 and a first end, e.g., a proximal end, of a first manipulator link 113. Yaw joint 111 allows first manipulator link 113 to move with reference to link 106 in a motion that may be arbitrarily defined as "yaw" around a manipulator assembly yaw axis 123. As shown, the rotational axis of yaw joint 111 is aligned with a remote center of motion 146, which is generally the position at which an instrument enters the patient (e.g., at the umbilicus for abdominal surgery).

In one embodiment, setup link 106 is rotatable in a horizontal or x, y plane and yaw joint 111 is configured to allow first manipulator link 113 in entry guide manipulator 130 to rotate about yaw axis 123. Setup link 106, yaw joint 111, and first manipulator link 113 provide a constantly vertical yaw axis 123 for entry guide manipulator 130, as illustrated by the vertical line through yaw joint 111 to remote center of motion 146.

A distal end of first manipulator link 113 is coupled to a proximal end of a second manipulator link 115 by a first actively controlled rotational joint 114. A distal end of second manipulator link 115 is coupled to a proximal end of a third manipulator link 117 by a second actively controlled rotational joint 116. A distal end of third manipulator link 117 is coupled to a distal portion of a fourth manipulator link 119 by a third actively controlled rotational joint 118.

In one embodiment, links 115, 117, and 119 are coupled together to act as a coupled motion mechanism. Coupled motion mechanisms are well known (e.g., such mechanisms are known as parallel motion linkages when input and output link motions are kept parallel to each other). For example, if rotational joint 114 is actively rotated, joints 116 and 118 are also actively rotated so that link 119 moves with a constant relationship to link 115. Therefore, it can be seen that the rotational axes of joints 114, 116, and 118 are parallel. When these axes are perpendicular to rotational axis 123 of joint 111, links 115, 117, and 119 move with reference to link 113 in a motion that may be arbitrarily defined as "pitch" around a manipulator assembly pitch axis. The manipulator pitch axis extends into and out of the page in FIG. 1 at remote center of motion 146, in this aspect. The motion around the manipulator assembly pitch axis is represented by arrow 121. Since links 115, 117, and 119 move as a single assembly in this embodiment, first manipulator link 113 may be considered an active proximal manipulator link, and second through fourth manipulator links 115, 117, and 119 may be considered collectively an active distal manipulator link.

An entry guide manipulator assembly platform 132, sometimes referred to as platform 132, is coupled to a distal end of fourth manipulator link 119. An entry guide manipulator assembly 133 is rotatably mounted on platform 132. Entry guide manipulator assembly 133 includes an instrument manipulator positioning system.

Entry guide manipulator assembly 133 rotates a plurality of instrument manipulators 140 as a group around axis 125. Specifically, entry guide manipulator assembly 133 rotates as a single unit with reference to platform 132 in a motion that may be arbitrarily defined as "roll" around an entry guide manipulator assembly roll axis 125.

Each of a plurality of instrument manipulators 140 is coupled to entry guide manipulator assembly 133 by a different insertion assembly 135. In one aspect, each insertion assembly 135 is a telescoping assembly that moves the corresponding instrument manipulator away from and towards entry guide manipulator assembly 130. In FIG. 1, each of the insertion assemblies is in a fully retracted position.

Each of the plurality of instrument manipulator assemblies includes a plurality of motors that drive a plurality of outputs in an output interface of that instrument manipulator. See U.S. Patent Application No. 61/866,115 (filed on 15 Aug. 2013), which is incorporated by reference, for one example of an instrument manipulator and a surgical instrument that can be coupled to the instrument manipulator.

In one aspect, a membrane interface that is part of a sterile surgical drape may be placed between the instrument mount interface of an instrument manipulator and the input interface of the transmission unit of a corresponding surgical instrument. See, for example, U.S. Patent Application Publication No. US 2011/0277776 A1 for an example of the membrane interface and sterile surgical drape. In another aspect, a sterile adapter that is part of a sterile surgical drape may be placed between the instrument mount interface of the instrument manipulator and the input interface of the transmission unit of the corresponding surgical instrument. See, for example, U.S. Patent Application Publication No. US 2011/0277775 A1 for an example of a sterile adapter and a sterile surgical drape.

FIGS. 2A and 2B illustrate perspective views of an example of a movable and/or detachable cannula mount 250 in a retracted position and a deployed position, respectively. Cannula mount 250 includes a linear extension 252, i.e., a straight arm, which is movably coupled to a link 219 of the manipulator arm, such as an end of fourth manipulator link 119 (FIG. 1). Cannula mount 250 further includes a clamp 254 on a distal end of linear extension 252.

In one implementation, linear extension 252 is coupled to link 219 by a rotational joint 253 that allows linear extension 252 to move between a stowed position adjacent link 219 (FIG. 2A) and an operational position (FIG. 2B) that holds the cannula in the correct position so that the remote center of motion is located along the cannula. In one implementation, linear extension 252 may be rotated upwards or folded toward link 219, as shown by arrow C (FIG. 2B), to create more space around the patient and/or to more easily drape the cannula mount when draping the manipulator arm.

SUMMARY

A surgical system includes a link of a manipulator arm and a telescoping cannula mount assembly. The link includes a curved end. The telescoping cannula mount assembly is positioned in the curved end of the link. The telescoping cannula mount assembly includes a curved cannula mount arm. In a first state, the curved cannula mount arm is parked within the curved end of the link. In a second state, the curved cannula mount arm extends from the curved end of the link and is locked in an extended position. The telescoping cannula mount assembly is configured to automatically move the curved cannula mount arm from the extended position to the parked position.

The telescoping cannula mount assembly also includes a mechanical arm retraction system. The mechanical arm retraction system couples the curved cannula mount arm to the curved end of the link. The mechanical arm retraction system is configured to automatically move the curved cannula mount arm from the second state to the first state. In one aspect, the curved cannula mount arm includes a bearing assembly that moves linearly along a curved rail that is affixed to the curved end of the link.

The mechanical arm retraction system includes a spring, a segment gear, a pinion gear, and a damper. The damper is coupled to the curved end of the link and is coupled to the curved cannula mount arm. The spring is coupled to the curved end of the link and is coupled to the curved cannula mount arm. The segment gear includes a first end and a second end. The first end of the segment gear is connected to the curved end of the link, and the second end of the segment gear is coupled to the spring. The pinion gear is coupled to the curved cannula mount arm. The pinion gear mates with the segment gear. The damper includes a shaft. The damper is connected to the curved cannula mount arm, and the pinion gear is mounted on the shaft of the damper.

The telescoping cannula mount assembly also includes a curved tray and a rolling loop electrical cable. The curved tray is connected to the curved end of the link. The rolling loop electrical cable includes a first end and a second end. The first end of the rolling loop electrical cable is connected to the curved cannula mount arm, and the second end of the rolling loop electrical cable is connected to the curved tray.

In one aspect, the curved cannula mount arm has a first end and a second end. The second end of the curved cannula mount arm is within the curved end of the link in the first state and in the second state. The telescoping cannula mount assembly also includes a latch and a latching/unlatching system. The latch is on the second end of curved cannula mount arm. When the curved cannula mount arm is in the extended position, the latching/unlatching system engages the latch to lock the curved cannula mount arm in the extended position.

The latching/unlatching system includes an electric actuator and a locking assembly connected to the electric actuator. In the extended position, the locking assembly engages the latch to lock the curved cannula mount arm in the extended position. If the electric actuator is activated, the locking assembly disengages from the latch so that the mechanical arm retraction system can automatically retract the curved cannula mount are into the link.

The telescoping cannula mount assembly also includes an interlock control system. The interlock control system includes an electric actuator bus, a bus dump circuit, and the electric actuator. The bus dump circuit and the electric actuator are connected between the electric actuator bus and a ground.

In one aspect, the curved cannula mount arm includes an arm retraction button and a cannula release button. In this aspect, the curved cannula mount arm has an outer surface and the arm retraction button has a surface. The arm retraction button is mounted in the curved cannula mount arm with the surface of the arm retraction button flush with the outer surface of curved cannula mount arm when the arm retraction button is not depressed. The cannula release button is configured to move linearly into the curved cannula mount arm with respect to the outer surface.

The surgical system also includes a cannula mount assembly. The cannula mount assembly includes a cannula docking assembly configured to dock a cannula, a linkage assembly, a cannula release button assembly having a first end and a second end, and a linear motion assembly. The cannula docking assembly is coupled to the first end of the cannula release button assembly by the linkage assembly. The second end of the cannula release button assembly is coupled to the linear motion assembly. The linear motion assembly is configured to constrain the cannula release button assembly to linear motion in first and second directions.

A method includes automatically configuring a manipulator arm assembly including a curved cannula mount arm for draping by withdrawing the curved cannula mount arm into a curved end of a link of the manipulator arm assembly by a mechanical arm retraction system in the curved end of the link.

Another method includes locking a curved cannula mount arm in an extended position from a curved link of a manipulator arm assembly by engaging a locking assembly coupled to the curved link with a latch on the curved cannula mount arm. This method also includes activating an electrical component coupled to the locking assembly to disengage the locking assembly from the latch. This method further includes inhibiting the activating of the electrical component if a cannula is docked to the curved cannula mount arm.

Figure 1:
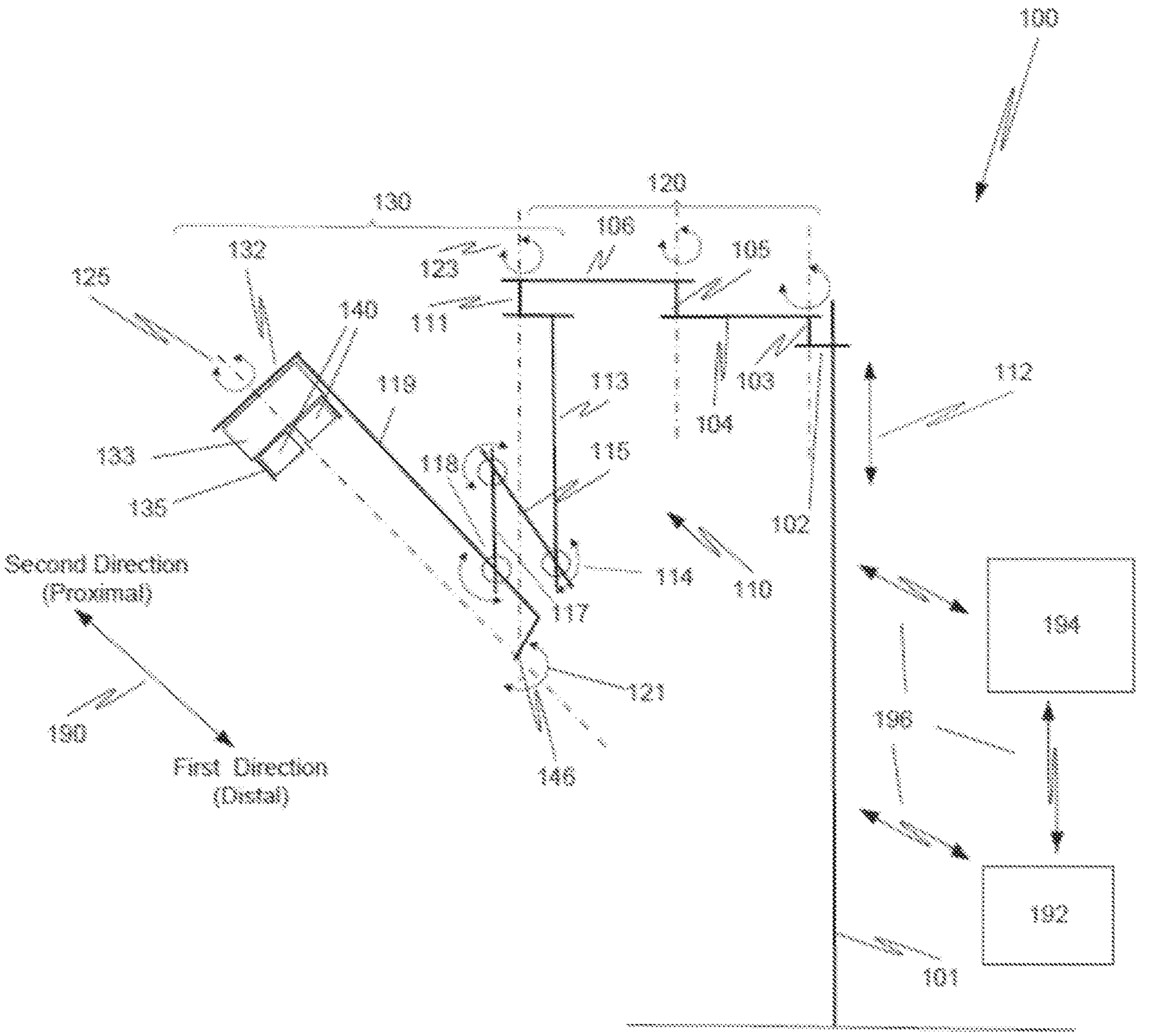
Fig. 1 (Prior Art)
FIG. 1 is a diagram of a prior art computer-assisted surgical system.

In general, in the drawings, the first digit of a three digit reference numeral is the figure number in which the element having that reference numeral first appeared. The first two digits of a four digit reference numeral are the figure number in which the element having that reference numeral first appeared.

DETAILED DESCRIPTION

Figure 3:
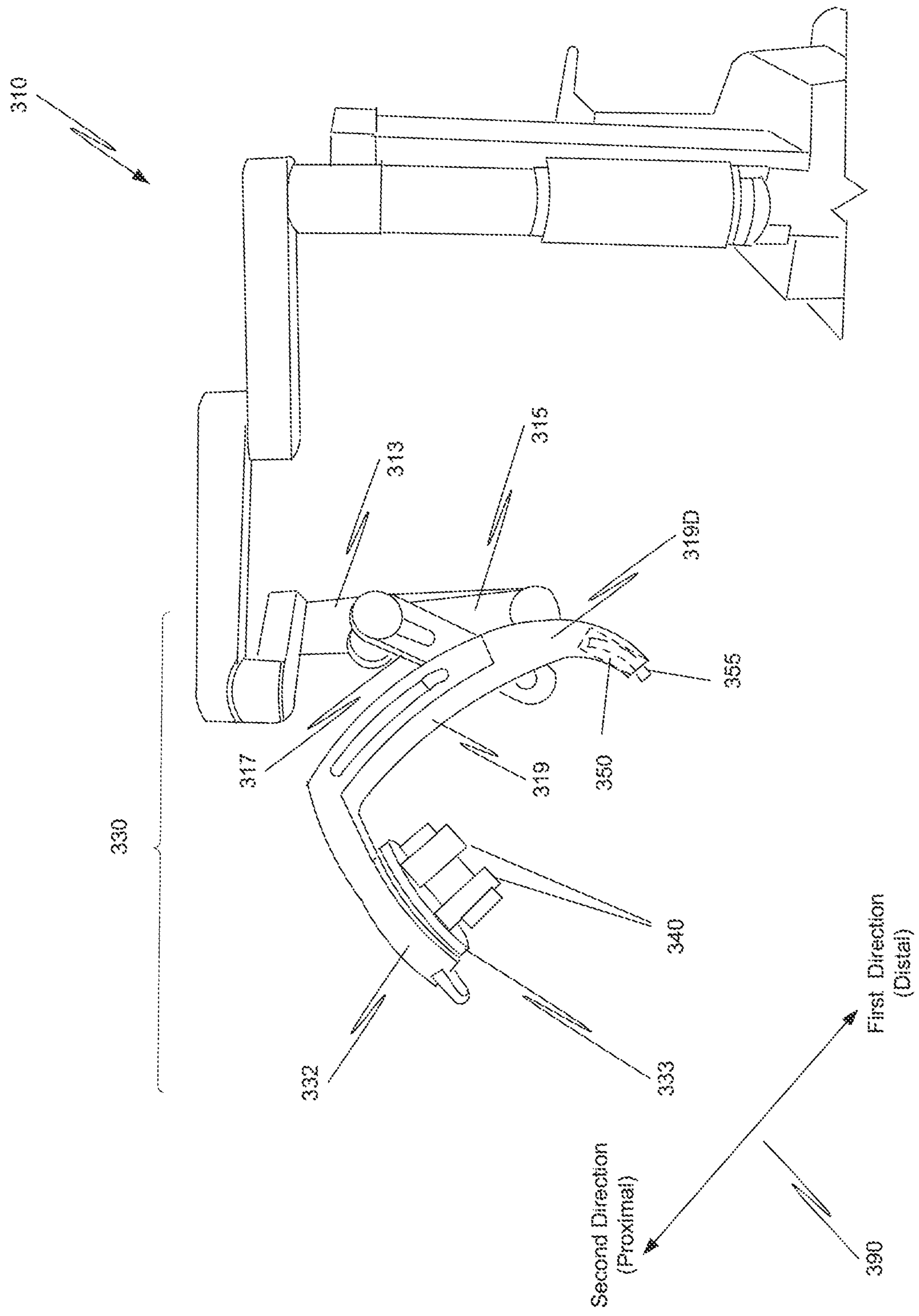
FIG. 3 is an illustration of a patient side support system with a telescoping cannula mount system.

FIG. 3 is an illustration of a patient side support system 310 in a computer-assisted surgical system that includes a telescoping cannula mount system 350, sometimes referred to as cannula mount system 350, in a curved distal end portion 319D of a fourth link 319 in a manipulator arm assembly 330. Telescoping cannula mount system 350 is configured to automatically move a curved cannula mount arm 355 of telescoping cannula mount system 350 from a position extending from fourth link 319 to a parked position within fourth link 319.

Arrow 390 shows the distal and proximal directions used in the discussion of FIG. 3. The proximal and distal directions are an example of a first direction and a second direction opposite to the first direction. The computer-assisted surgical system includes a controller, an imaging system and a surgeon's console-all of which are coupled to patient side support system 310.

In this aspect, some parts of manipulator arm assembly 330 are equivalent to corresponding parts in patient side support system 110 in FIG. 1. In particular, links 113, 115, 117, 119, manipulator arm assembly 130, and plurality of instrument manipulators 140 are equivalent to links 313, 315, 317, 319, manipulator arm assembly 330, and plurality of instrument manipulators 340, respectively, with the exceptions described in more detail below. In particular, link 319 has a curved distal end portion 319D that includes a telescoping cannula mount system 350, described herein. Thus, the description associated with FIG. 1 is not repeated here for FIG. 3, but is incorporated herein by reference.

Curved cannula mount arm 355, sometimes referred to as arm 355 or as cannula mount arm 355, is moveably mounted in telescoping cannula mount system 350. In FIG. 3, patient side support system 310 is configured for mounting a sterile surgical drape on plurality of instrument manipulators 340 and manipulator arm assembly 330. In particular, curved cannula mount arm 355 is retracted into curved distal end portion 319D of link 319, e.g., cannula mount arm 355 is parked within link 319. This is a first state of cannula mount arm 355, in which cannula mount system 350 has no stored potential energy that can be used to move cannula mount arm 355. When cannula mount arm 355 is parked, cannula mount arm 355 is said to be in a first state.

Manipulator arm assembly 330 is covered with a sterile drape, by sliding the drape over all links, starting with plurality of instrument manipulators 340, entry guide manipulator assembly 333 and entry guide manipulator assembly platform 332, and sliding to the proximal end of first manipulator link 313. With cannula mount arm 355 in the parked position, draping is easier, in particular when passing the drape over links 319, 317 and 315, because the effective width of the system at this point is narrower with cannula mount arm 355 in the parked position. The drape sleeve for cannula mount arm 355 does not have to be positioned about cannula mount arm 355 to enable the complete draping of links 319 to 313. A cannula mount sterile adapter is mounted on a first end of cannula mount arm 355 that protrudes from a distal face of curved distal end portion 319D of link 319. For an example of a cannula sterile adapter suitable for use with cannula mount arm 355, see PCT International Publication No. PCT/US2015/020916 A1 (published on 24 Sep. 2015 as WO2015/142814; disclosing "Surgical Cannula Mounts and Related Systems and Methods"), which is incorporated herein by reference.

Figure 2A:
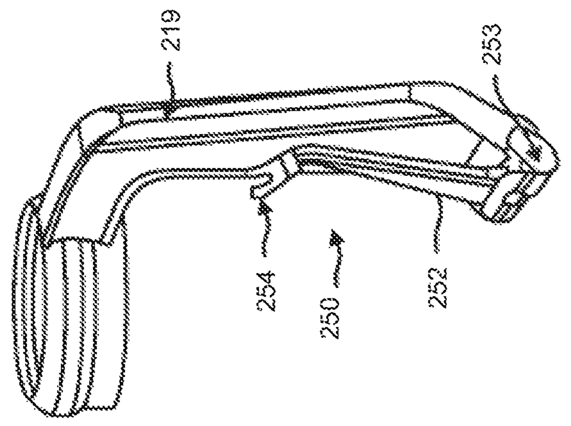
Fig. 2A (Prior Art)
FIGS. 2A and 2B illustrate perspective views of an example of a prior art movable and/or detachable cannula mount in a retracted position and a deployed position, respectively.
Figure 2B:
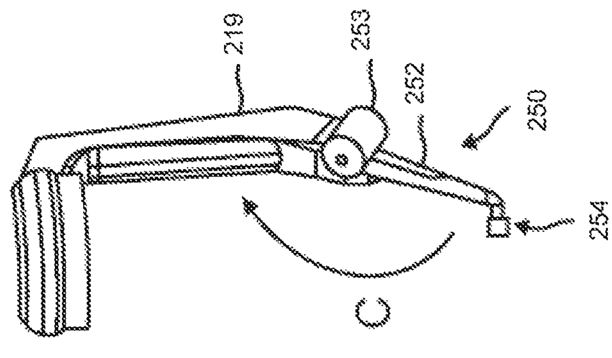
Fig. 2B (Prior Art)

With cannula mount arm 355 parked, it allows the person doing the draping to move around curved distal end portion 319D of link 319 without worrying about snagging the drape on cannula mount arm 355, and it provides more unencumbered space for that person to work. This is narrower than a system that has a folded linear cannula mount arm during the draping process. (See FIG. 2B). Moreover, curved cannula mount arm 355 permits retracting arm 355 further into curved distal end portion 319D of link 319 than would be possible if the prior art linear arm were retracted into curved distal end portion 319D of link 319.

In some aspects, to dock a cannula to the first end of cannula mount arm 355, cannula mount arm 355 must be in an extended and locked position. To extend cannula mount arm 355 from curved distal end portion 319D of link 319, a user grasps the first end of cannula mount arm 355 and pulls cannula mount arm 355 from the distal end of link 319.

As cannula mount arm 355 is pulled from the distal end of link 319, the motion of arm 355 stores energy in an arm retraction system within telescoping cannula mount system 350. When cannula mount arm 355 locks in the extended position, telescoping cannula mount system 350 stores sufficient potential energy to automatically retract cannula mount arm 355 back to the parked position.

In one aspect, telescoping cannula mount system 350 is used to automatically configure manipulator arm assembly 330 for draping by automatically retracting cannula mount arm 355 to the parked position within curved distal end portion 319D of link 319. However, as explained more completely below, when cannula mount arm 355 is locked in the extended position and a cannula is docked to cannula mount arm 355, a controller of telescoping cannula mount system 350 inhibits unlocking of cannula mount arm 355 until cannula mount arm 355 can be safely retracted back into curved distal end portion 319D of link 319.

The arm retraction system of telescoping cannula mount system 350 does not include an electrical motor to retract cannula mount arm 355. The arm retraction system provides an automatic smooth controlled retraction of cannula mount arm 355 without extra motors without the extra electronics, and sensors required to safely implement a motorized axis. Thus, there is no possibility that an electrical short, an induced current, or any other source of electrical power can inadvertently cause such an electrical motor to move cannula mount arm 355 during a surgical procedure. The arm retraction system is referred to as a mechanical arm retraction system to indicate that the arm retraction system includes only mechanical components and no electrical components such as a motor, electronics or electrical components.

An electrical component, e.g., an electric actuator, in a latching/unlatching system is used to unlatch cannula mount arm 355 so that potential energy in the mechanical arm retraction system automatically retracts cannula mount arm 355. As indicated above, the mechanism of mechanical arm retraction system is entirely mechanical and so there is no potential for an electrical problem affecting the operation of mechanical arm retraction system.

However, if the electrical component in the latching/unlatching system were inadvertently fired during a surgical procedure, the mechanical arm retraction system would retract cannula mount arm 355. The normal fault recovery logic in a computer-assisted surgical system would not be able to compensate for such an inadvertent firing of the electrical component in the latching/unlatching system. Thus, in one aspect, the power to trigger this electrical component is shorted to ground during a surgical procedure. Consequently, use of the electrical component in the latching/unlatching system is inhibited during a surgical procedure. Any spurious voltage on the power line to the electrical component is also shorted to ground, and this assures that the electrical component cannot be fired during the surgical procedure, and so cannula mount arm 355 cannot be inadvertently retracted from the locked and extended position.

Figure 4B:
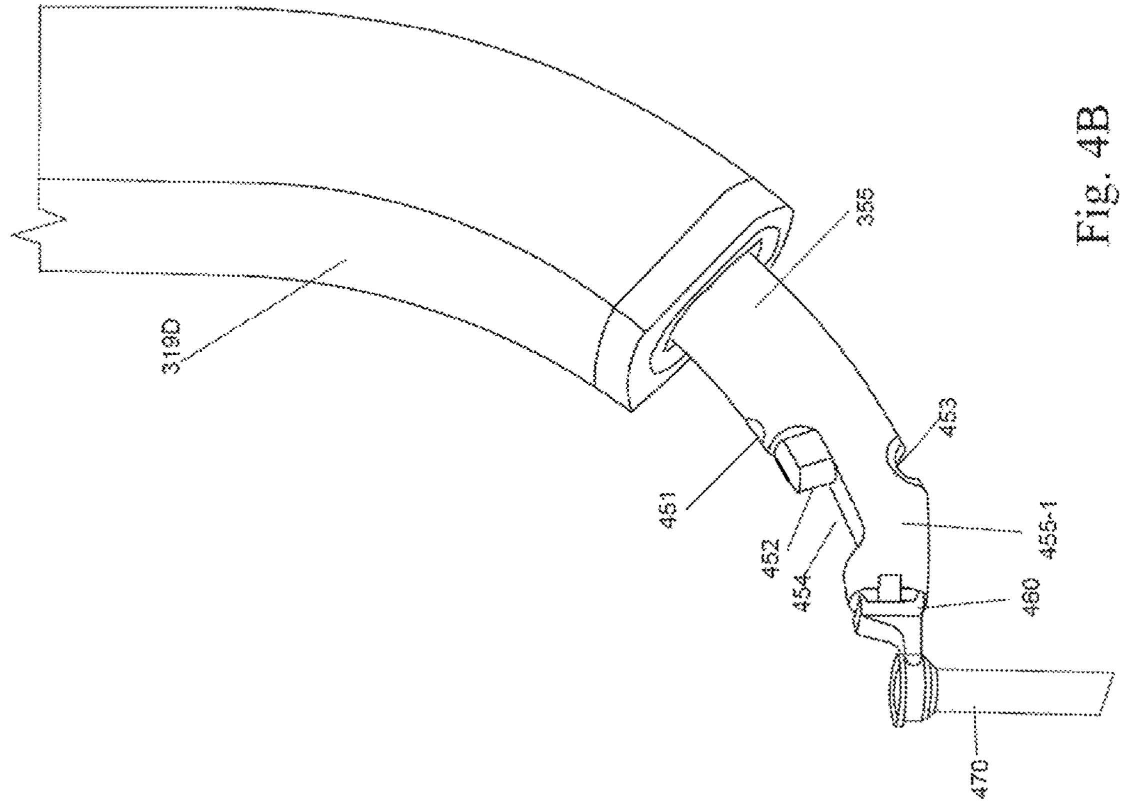
FIG. 4B is a perspective view of the curved distal end portion of the fourth link of the patient side support system of FIG. 3 with the curved cannula mount arm extending from the curved distal end portion and locked in the extended position.
Figure 4A:
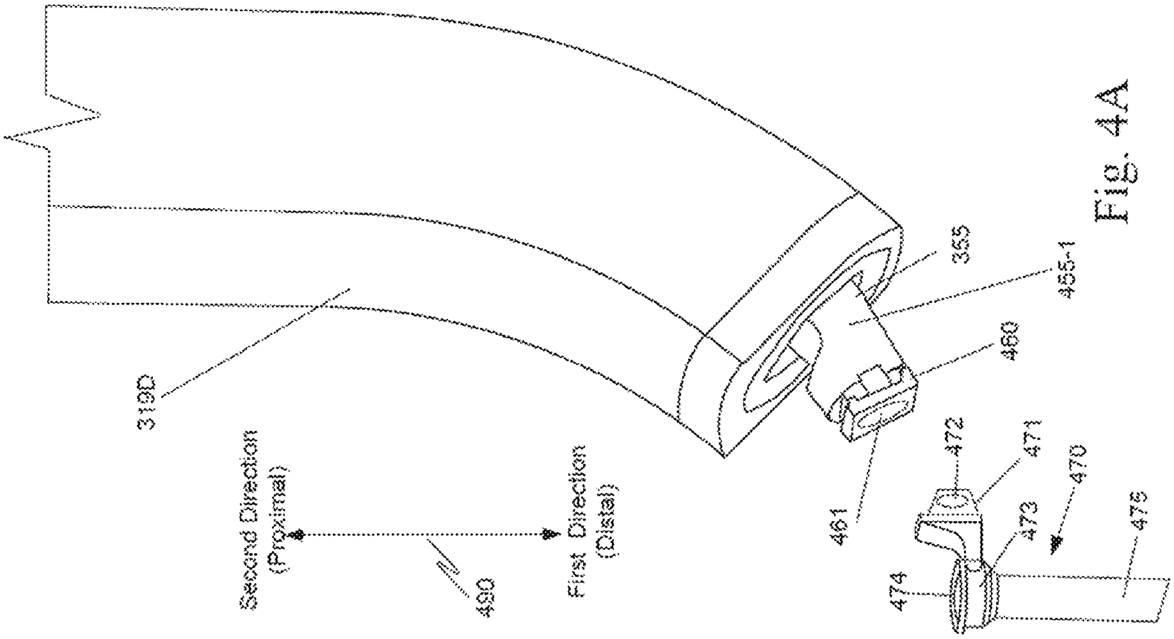
FIG. 4A is a perspective view of the curved distal end portion of a fourth link of the patient side support system of FIG. 3 with a curved cannula mount arm retracted, e.g., parked, in the curved distal end portion.

FIGS. 4A and 4B are enlarged illustrations of curved distal end portion 319D of fourth link 319. In FIGS. 4A and 4B, arrow 490 shows the first and second directions used in the discussion of FIGS. 4A and 4B. The proximal and distal directions are an example of a first direction and a second direction opposite to the first direction.

In particular, FIG. 4A is a perspective view of curved distal end portion 319D of fourth link 319, sometimes referred to as link 319, with curved cannula mount arm 355 retracted, e.g., parked. In the parked position, telescoping cannula mount system 350 has no stored potential energy that can move cannula mount arm 355, and so telescoping cannula mount system 350 and cannula mount arm 355 are said to be in a zero energy state, which was referred to as the first state above. When cannula mount arm 355 is parked in curved distal end portion 319D of fourth link 319, a portion of a first end 455-1 of cannula mount arm 355 extends from a distal face of curved distal end portion 319D of link 319.

Cannula sterile adapter 460 is shown mounted on first end 455-1 of cannula mount arm 355. In this example, cannula sterile adapter 460 includes an aperture 461 configured to receive an attachment portion 471 of cannula 470. While it not shown in the drawings, cannula sterile adapter 460 typically is attached to a surgical drape to facilitate forming a boundary between a sterile region and a non-sterile region.

In this example, cannula 470 includes a bowl section 473 at a proximal end 474 of cannula 470. A tube 475 extends in a distal direction from bowl section 473. Attachment portion 471 is attached to bowl section 473. Attachment portion 471 may include depressions 472 on opposite sides of attachment portion 471 to assist with mounting cannula 470 to a cannula mount assembly (see FIGS. 10 and 11) in the distal end, first end 455-1, of cannula mount arm 355. Depressions 472 are configured to facilitate docking of cannula 470 to cannula sterile adapter 460 and the cannula mount assembly. For examples of cannula 470 suitable for use with cannula mount arm 355, see PCT International Publication No. PCT/US2015/020916 A1.

To attach cannula 470 to cannula mount arm 355, cannula mount arm 355 must first be withdrawn from curved distal end portion 319D of distal link 319 and locked in an extended position, and then cannula 470 can be docked at the distal end of cannula mount arm 355. Since telescoping cannula mount system 350 does not include any electrical motors, cannula mount arm 355 must be manually withdrawn from curved distal end portion 319D.

Thus, a person grasps first end 455-1 of cannula mount arm 355 and pulls cannula mount arm 355 from curved distal end portion 319D. The force used to pull cannula mount arm 355 from curved distal end portion 319D is stored by telescoping cannula mount system 350 as potential energy that can be used later to automatically retract cannula mount arm 355. When cannula mount arm 355 is fully extended, cannula mount arm is locked in the extended position, as illustrated in FIG. 4B. When cannula mount arm 355 is locked in the extended position, e.g., locked in a second state of the arm, a cannula arm extended and locked signal is sent to the controller.

Cannula mount arm 355 includes a plurality of buttons. In one aspect, the plurality of buttons includes an arm retraction button 451, a cannula release button 452, and a clutch button 453. If cannula 470 is not docked on cannula mount arm 355, depressing arm retraction button 451 causes cannula mount arm 355 to be automatically retracted into curved distal end portion 319D of link 319.

The shape of cannula mount arm 355 and the configuration of the plurality of buttons are selected so that when cannula mount arm 355 is retracted into curved distal end portion of link 319 while draped, it unlikely that drape will be snagged or caught on any of the plurality of buttons or any part of cannula mount arm 355. This prevents a contaminated drape from being pulled inside curved distal end portion 319D of link 319 and potentially damaged. Thus, the interior of link 319 does not require sterilization before use in another surgical procedure.

In this aspect, a portion of cannula mount arm 355 has an oval shape and there are no abrupt changes in shape of cannula mount arm 355 on which a surgical drape could be caught. When it is said the cannula mount arm 355 has an oval shape, it means that in a cross-sectional view, the outer surface of cannula mount arm 355 has an oval shape.

In particular, edges of indentation 454 are sloped and curved so that the surgical drape slides over the edges of indentation 454 as cannula mount arm 355 is retracted. Similarly, a surface of arm retraction button 451 is flush with the outer surface of cannula mount arm 355, when not depressed, so that there is no edge of arm retraction button 451 to snag the drape as the drape moves across arm retraction button 451.

Cannula release button 452 has smooth edges and surfaces so that if the drape falls into indentation 454, the drape moves smoothly around cannula release button 452 as cannula mount arm 355 retracts. The surface and curvature of clutch button 453 is similarly selected so that there are no edges or abrupt surface changes that could snag the drape as cannula mount arm 355 retracts.

If cannula 470 is not docketed on cannula mount arm 355, the controller inhibits entering a following system mode of operation. In the following system mode of operation, sometimes referred to as following, motion of a slave surgical instrument follows motion of a master tool teleoperatively coupled to the slave surgical instrument.

To mount cannula 470 on cannula mount arm 355, both cannula release button 452 and clutch button 453 are depressed simultaneously and held in the depressed position. Manipulator arm assembly 330 is moved, while clutched, to the location of attachment portion 471 of cannula 470, and then attachment portion 471 is inserted into cannula sterile adapter 460 and into the distal end of cannula mount arm 355. Then, cannula release button 452 and clutch button 453 are released and cannula 470 is latched to cannula mount arm 355, which is now no longer clutched, but is now locked in place. In order to facilitate one-person docking, the two buttons 452 and 453 are positioned to allow operation with one hand, while the second hand can be used to hold cannula 470 in the proper orientation for docking.

In one aspect, there are sensors in the cannula mounting system that indicate when a cannula is docked to cannula mount arm 355. When the controller receives a signal that a cannula is docked to cannula mount arm 355, the controller disables the retraction of cannula mount arm 355. The retraction of cannula mount arm 355 remains disabled until after cannula 470 is undocked from cannula mount arm 355. Specifically, depressing arm retraction button 451 after cannula 470 is docked results in no action. Similarly, the controller cannot successfully command retraction of cannula mount arm 355 until after cannula 470 is undocked.

As explained more completely below, cannula release button 452 is purely mechanical, and if cannula release button 452 is depressed, cannula 470 will be free to be pulled out of the cannula mount assembly. The same thing is true in docking cannula 470, if cannula release button 452 is depressed, cannula 470 can be positioned in the cannula mount assembly. Therefore, clutch button 453 does not always have to be pressed to dock cannula 470—for example, if the cannula mount arm 355 could be clutched to the exact proper location, then cannula 470 could be docked using only cannula release button 452. However, typically, both buttons 452 and 453 are activated simultaneously, because otherwise, it is hard to tell when cannula 470 and the cannula mount assembly are properly aligned.

Figure 5B:
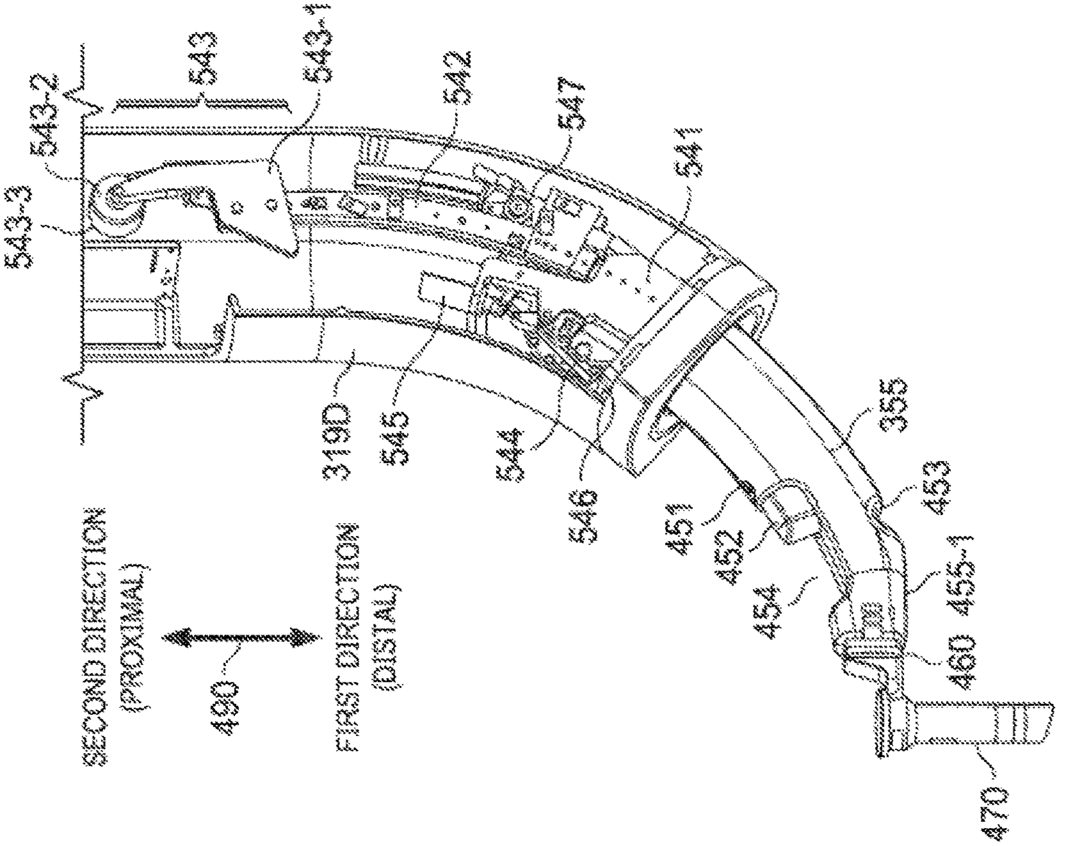
FIG. 5B a perspective cut away view of the curved distal end portion of the fourth link of the patient side support system of FIG. 3 with the curved cannula mount arm in the extended position to show the cannula mount system that includes the mechanical arm retraction system and the latching/unlatching system.
Figure 5A:
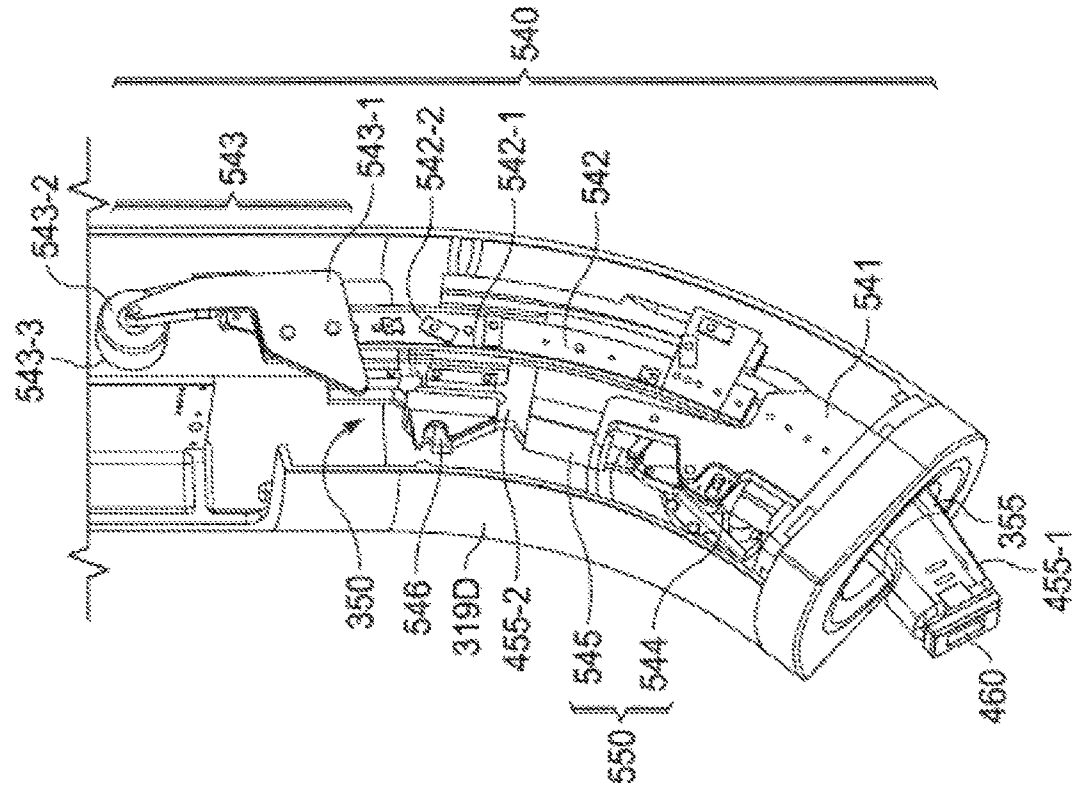
FIG. 5A a perspective cut away view of the curved distal end portion of the fourth link of the patient side support system of FIG. 3 with the curved cannula mount arm parked to show a cannula mount system that includes a mechanical arm retraction system and a latching/unlatching system.

FIGS. 5A and 5B are cutaway illustrations of curved distal end portion 319D of link 319 to show cannula mount system 350 that includes mechanical arm retraction system 540 and a latching/unlatching system 550. Mechanical arm retraction system 540 includes a constant force spring 543-3, a pinion gear 547 coupled to a rotary damper 648 (FIG. 6A), and a curved segment gear 542. Latching/unlatching system 550 includes a solenoid 545 and a locking assembly 544. Solenoid 545 is an example of an electric actuator. In view of this disclosure, electric actuators other than a solenoid can be included in latching/unlatching system 550.

When latch 546 is released by latching/unlatching system 550, constant force spring 543-3 pulls cannula mount arm 355 in the second direction (the proximal direction in FIGS. 5A and 5B), i.e., automatically retracts cannula mount arm 355 into curved distal end portion 319D of link 319. However, the speed of the retraction is limited by rotary damper 648, sometimes referred to as damper 648. Pinion gear 547 rides on curved segment gear 542 and is coupled to cannula mount arm 355 by rotary damper 648. Thus, as cannula mount arm 355 is moved in the second direction, pinion gear 547 rotates, but the speed of the rotation is limited by rotary damper 648. This limits the speed that pinion gear 547 can move along curved segment gear 542. Consequently, cannula mount arm 355 is automatically retracted into curved distal end portion 319D of link 319 in a controlled manner, without use of any electric motor, electronics, or sensors.

An anchor bracket 541 is rigidly affixed to the distal end of curved distal end portion 319D. A first end, e.g., a distal end, of curved segment gear 542 is fixedly attached to anchor bracket 541. In this example, curved segment gear 542 is a curved rectangular-shaped arm with a first curved surface 542-1 and a second curved surface 542-2 opposite and removed from first curved surface 542-1. First curved surface 542-1 has a smaller radius of curvature than second curved surface 542-2. Second curved surface 542-2 includes gear teeth 642 in this example. See FIGS. 6A and 6B for a more detailed illustration of curved segment gear 542.

In another aspect, the gear teeth of curved segment gear 542 could be on first curved surface 542-1 or on one of the other sides of curved segment gear 542. Thus, the configuration of curved segment gear 542 in the drawings is optional and is not intended to be limiting to the specific configuration illustrated.

A spring assembly 543 includes a spring assembly bracket 543-1, a spool assembly 543-2, and a constant force spring 543-3. A first end, e.g., a distal end, of spring assembly bracket 543-1 is fixedly attached to a second end, e.g., a proximal end, of curved segment gear 542. Spool assembly 543-2 is mounted on a second end, e.g., a proximal end, of spring assembly bracket 543-1. Constant force spring 543-3, sometimes referred to as spring 543-3, is a metal spring. A second end of spring 543-3 is coiled onto spool assembly 543-2 so that spring 543-3 winds and unwinds around spool assembly 543-2. A first end of spring 543-3 is anchored to a second end 455-2, e.g., a proximal end, of cannula mount arm 355. Thus, as cannula mount arm 355 is withdrawn from curved distal end portion 319D, spring 543-3 is unwound from spool assembly 543-2, and so stores potential energy.

Second end 455-2, e.g., the proximal end, of cannula mount arm 355 includes a latch 546. In one aspect, latch 546 is mounted on second end 455-2 of cannula mount arm 355. In this aspect, latch 546 includes an inclined ramp that leads to a socket. (See FIG. 7B).

The electric actuator, e.g., solenoid 545, in latching/unlatching system 550 is mounted on anchor bracket 541. In this example, solenoid 545 is mounted on a second end of anchor bracket 541, where the first end of anchor bracket 541 is attached to curved distal end portion 319D. The solenoid plunger is connected to a locking assembly 544 in latching/unlatching system 550.

Locking assembly 544 engages latch 546 when cannula mount arm 355 is moved to the fully extended position as illustrated in FIG. 4B. To disengage locking assembly 544 from latch 546 so that spring 543-3 can retract curved cannula mount arm 355 into curved distal end portion 319D of link, solenoid 545 is activated, e.g., fired. As explained more completely below, when cannula mount arm 355 is locked in the extended position and cannula 470 is docked on cannula mount arm 355, firing of solenoid 545 is inhibited, and so cannula mount arm 355 cannot be retracted when a cannula is docked to arm 355.

Figure 6A:
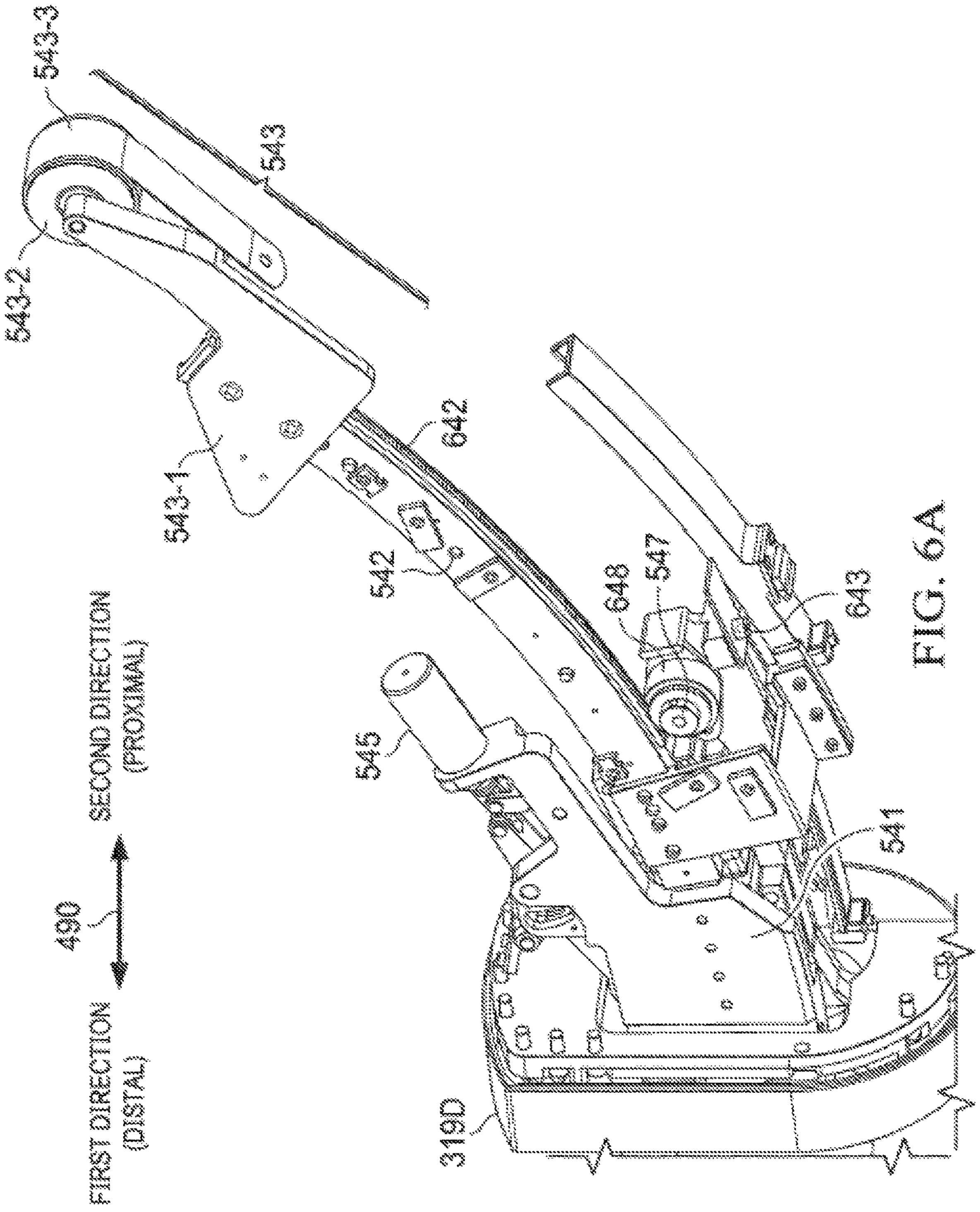
FIGS. 6A and 6B are opposing perspective side views of portions of the telescoping cannula mount system.
Figure 6B:
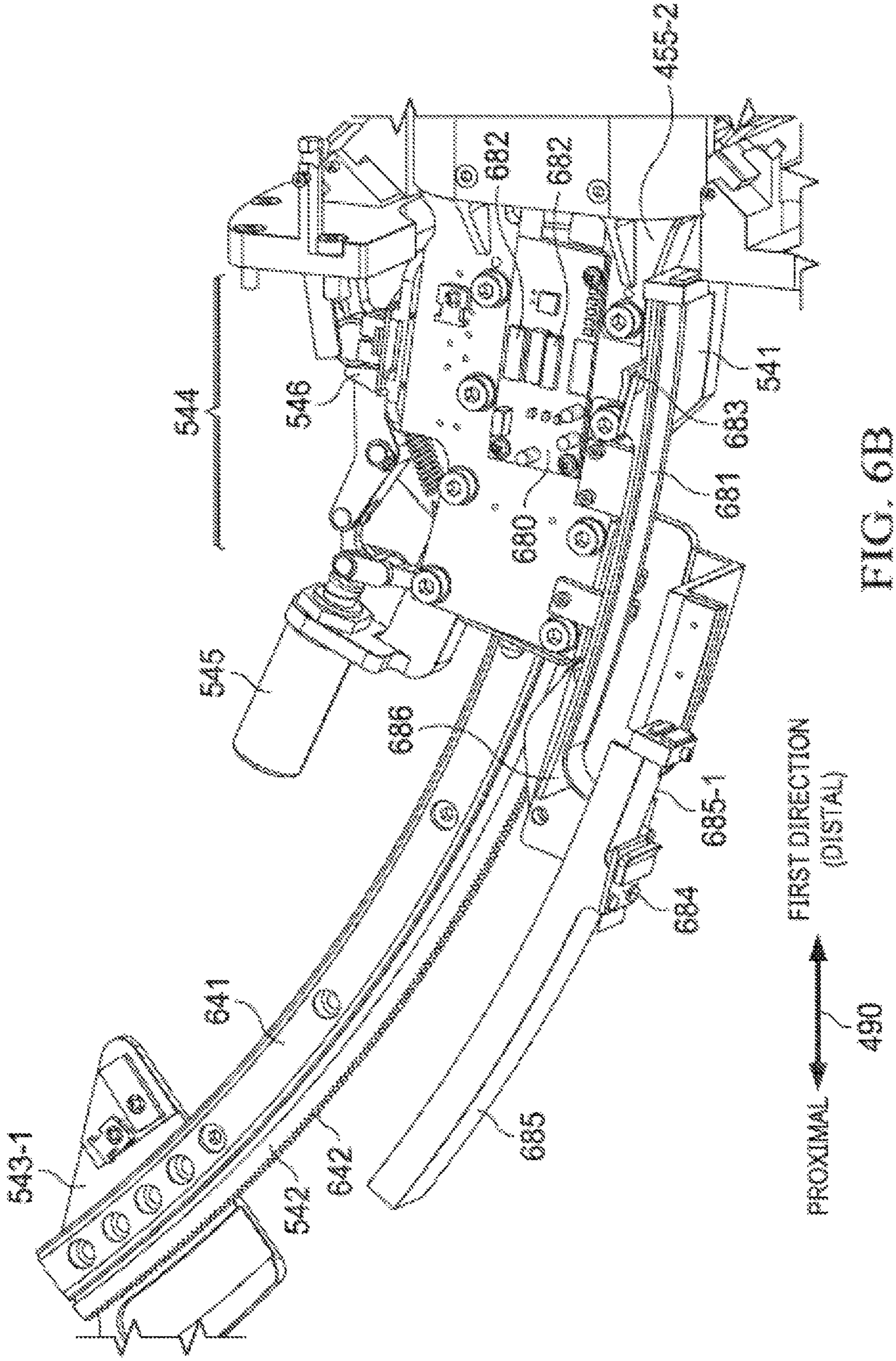

FIGS. 6A and 6B are opposing perspective side view of portions of telescoping cannula mount system 350. FIG. 6A shows that in this aspect, first end of spring 543-3 is fixedly attached to second end 455-2 of cannula mount arm 355 at point 643. Thus, FIG. 6A shows the first end of spring 543-3 both attached and unattached.

FIG. 6A also shows more clearly gear teeth 642 on second curved surface 542-2 of curved segment gear 542. Curved segment gear 542 is attached to a curved rail 641 (FIG. 6B). A plurality of bearing blocks, which are attached to cannula mount arm 355, ride on curved rail 641. A curved rail and associated bearing blocks suitable for use in telescoping cannula mount system 350 are commercially available from THK America, Inc., 200 East Commerce Drive, Schaumburg, IL. 60173 U.S.A.

Pinion gear 547 (FIGS. 5B and 6A) is attached to a rotating shaft of damper 648 (FIG. 6A). The teeth on pinion gear 547 mesh with gear teeth 642 of curved segment gear 542. Damper 648 is affixed to second end 455-2 of cannula mount arm 355. Damper 648 provides no damping when cannula mount arm 355 is manually withdrawn, i.e., extended, from curved distal end portion 319D. Damper 648 provides damping as spring 543-3 automatically retracts cannula mount arm 355 into curved distal end portion 319D. The amount of damping is selected so that cannula mount arm does not suddenly snap back into curved distal end portion 319D, but retracts with a controlled safe speed with low impact at the end of travel.

FIG. 6B shows locking assembly 544 in more detail. A circuit board 680 (FIG. 6B) is attached to second end 455-2 of cannula mount arm 355. Circuit board 680 is coupled to a latch sensor that is described below (see latch sensor 748 (FIG. 7A)), and to all other sensors and switches on cannula mount arm 355. To provide power to the latch sensor and to transfer signals from the circuit board 680 back to the controller, ribbon cables 681 are connected to circuit board 680. Ribbon cables 681 are an example of a rolling loop electrical cable. The use of more than one ribbon cable is optional. In some applications, a single ribbon cable could be used.

In this aspect, ribbon cables 681 are stacked beneath a cross-curve spring, i.e., are coupled to a spring. The cross-curve spring prevents ribbon cables 681 from buckling as the rolling loop formed by ribbon cables 681 deploys when cannula mount arm 355 moves into and out of curved distal end portion 319D. Thus, the electrical cable is coupled to a spring to prevent the electrical cable from buckling as the rolling loop formed by the electrical cable deploys The rolling loop formed by ribbon cables 681 is placed between two concentric trays 685 and 686.

In one aspect, ribbon cables 681 include a first plurality of ribbon cables and a second plurality of ribbon cables. The first plurality of ribbon cables carry signals to and from cannula mount system 350 and provide power to cannula mount system 350. The second plurality of ribbon cables form a ground bond between cannula mount arm 355 and link 319.

First ends of the first plurality of ribbon cables are attached to first connectors 682 that mate with first circuit board 680 of cannula mount arm 355. Second ends of the first plurality of ribbon cables are attached to a second circuit board within link 319 (the second circuit board is not shown). In one aspect, the second plurality of ribbon cables, e.g., two ribbon cables, is stacked beneath the first plurality of ribbons cables. The second plurality of ribbon cables is used as a ground bond between stationary link 319 and moving cannula mount arm 355. The second plurality of ribbon cables runs between connectors 683 and 684. Connector 683 is connected to cannula mount arm 355 and connector 684 is connected of second curved tray 685. Curved tray 685 is coupled to anchor bracket 541, and so is coupled to curved distal end portion 319D of link 319.

Thus, telescoping cannula mount system 350 includes a first curved tray 686 and a second curved tray 685. Second curved tray 685 is connected to the curved distal end portion 319D of link 319. First curved tray 686 is connected to the proximal end of cannula mount arm 355.

Rolling loop ribbon cables 681 are anchored between a first end 685-1—a distal end—of second curved tray 685 and a first end—a distal end—of first curved tray 686. A first portion of ribbon cables 681, e.g., a first leg, follows the curve of first curved tray 686 and then ribbon cables 681 have a shape resembling a letter "U" on its side. The U-shape forms a transition to a second portion of ribbon cables 681, e.g., a second leg that follows the curve of second curved tray 685. Thus, ribbon cables 681 form an open loop with both legs of the loop being curved and the length of each leg changing as cannula mount arm 355 is withdrawn and as cannula mount arm 355 is retracted.

Figure 7A:
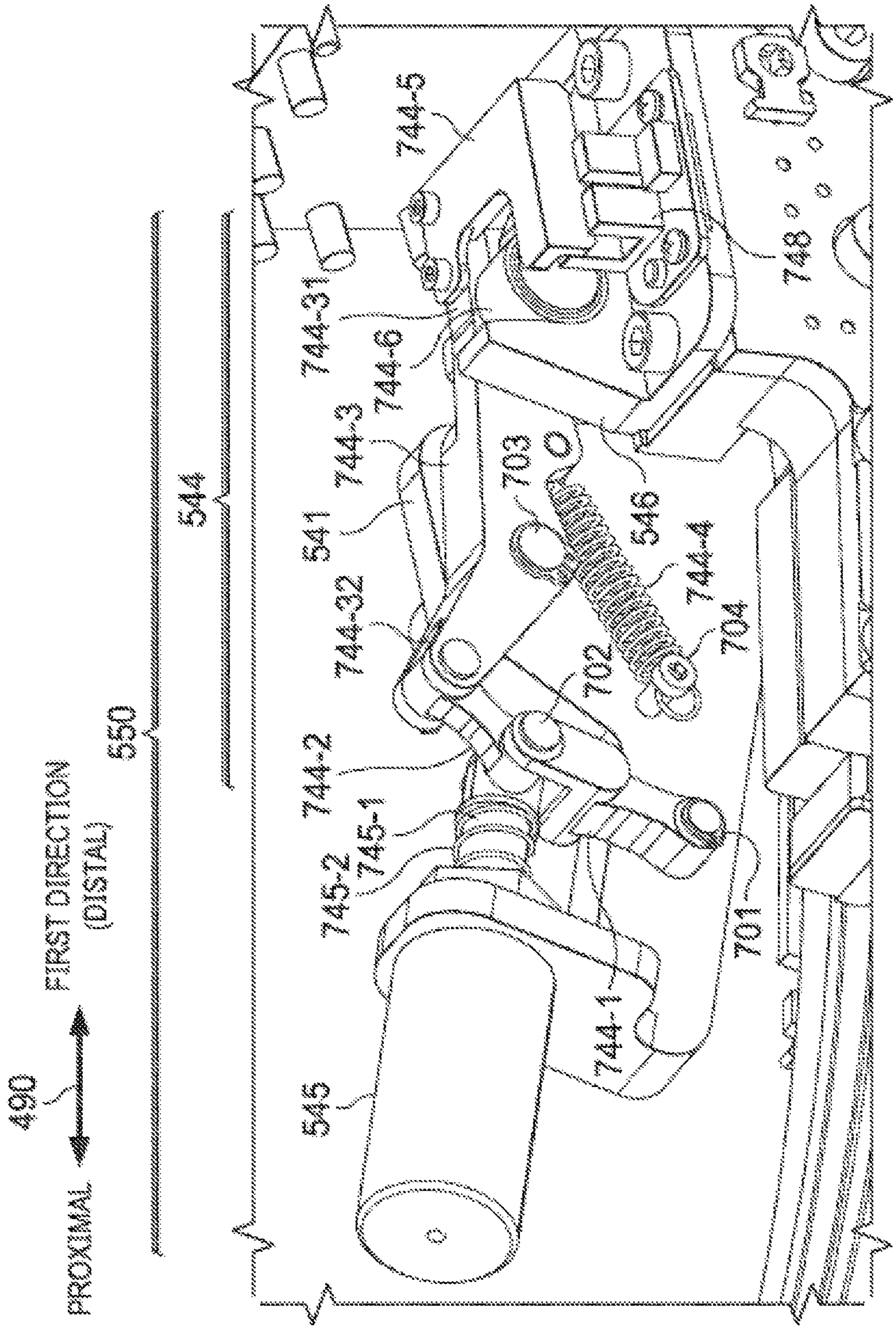
FIG. 7A is a perspective side view of a portion of the telescoping cannula mount system showing a latching/unlatching system and a latch.
Figure 7B:
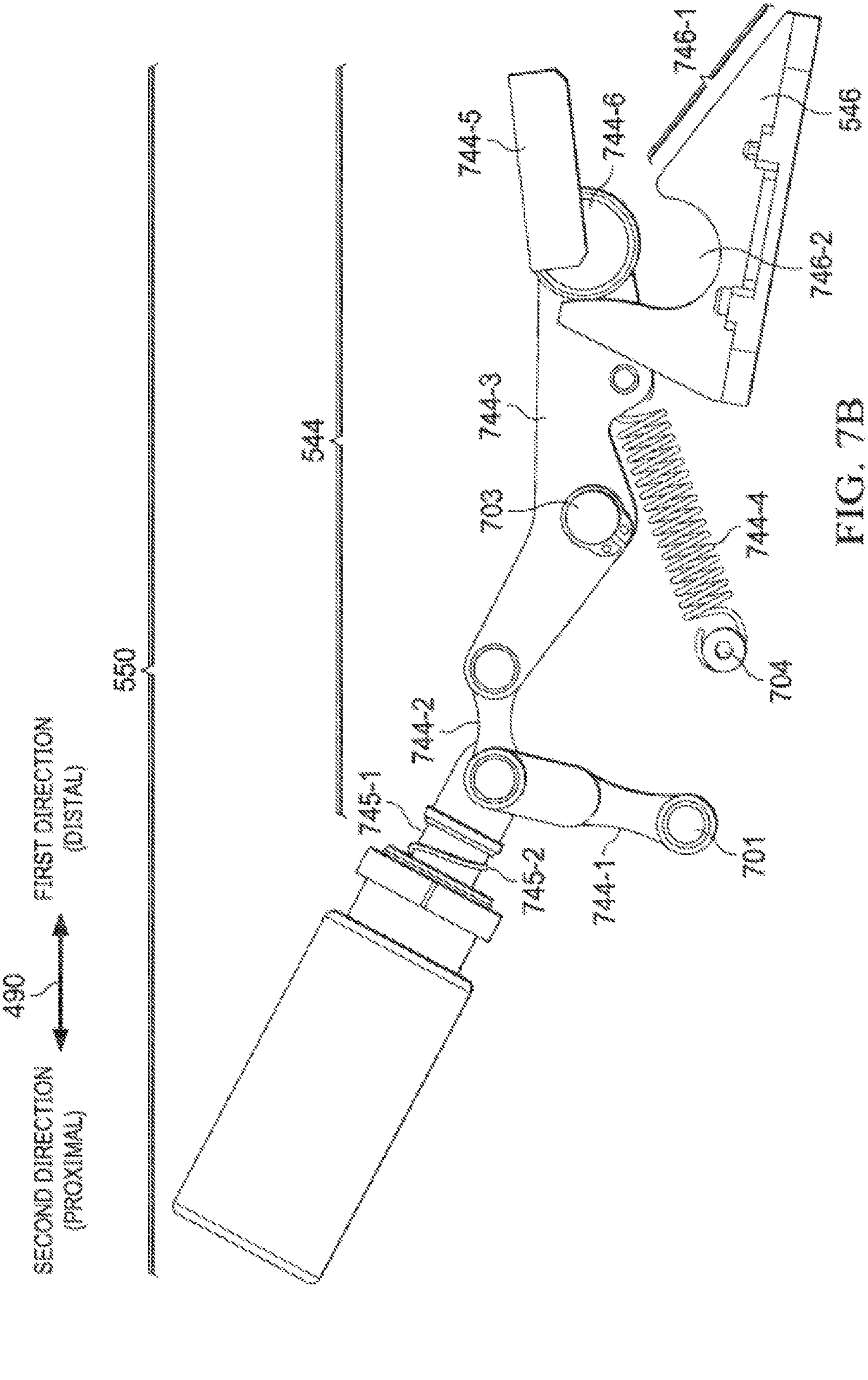
FIG. 7B is a view of the latching/unlatching system and the latch.

FIGS. 7A and 7B are more detailed illustrations of locking assembly 544 and latch 546. In this aspect, locking assembly 544 includes a first link 744-1, a second link 744-2, a latch link 744-3, a spring 744-4, a cam follower 744-6, and a latch flag 744-5.

First link 744-1 has a Y-shaped body. A second end of first link 744-1, which forms the base leg of the Y-shape, is rotatably mounted on a first pin 701 extending from anchor bracket 541. Thus, first link 744-1 is grounded to anchor bracket 541. A pin 702 extends between two legs at a first end of first link 744-1—the two legs forming the uprights of the Y-shape.

A plunger 745-1 of solenoid 545 is connected to pin 702. In this aspect, solenoid 545 is a linear motion solenoid, and plunger has a slot in one end. The slot rides on pin 702. A spring 745-2 around plunger 745-1 returns plunger 745-1 to the extended position after solenoid 545 is activated and then deactivated. Spring 745-2 and spring 744-4 work in the same direction, thus the forces of these two springs are additive.

A second end of second link 744-2 is rotatably mounted on pin 702, i.e., second link 744-2 is rotatably connected to first link 744-1. A first end of second link 744-2 is rotatably connected to a second end 744-32 of latch link 744-3.

Latch link 744-3 is mounted on a second pin 703 that extends from anchor bracket 541 between first end 744-31 and second end 744-32. Second pin 703 functions as a fulcrum (pivot point) for latch link 744-3. Latch link 744-3 is grounded to anchor bracket 541 by second pin 703. Cam follower 744-6 is affixed to a first side of a first end 744-31 of latch link 744-3. Latch flag 744-5 is affixed to a second side of the first end 744-31 of latch link 744-3. In this aspect, the first side and the second side of latch link 744-3 intersect to form one edge of latch link 744-3 that extends from the first end to the second end.

Thus, in this aspect, latch link 744-3 is implemented as a V-shaped lever with a first leg that extends from the pivot point to first end 744-31 and a second leg that extends from the pivot point to second end 744-32. The first leg is longer than the second leg in this aspect.

In this example, latch link 744-3 is a Class 1 lever because the fulcrum is between the effort (the force supplied by solenoid 545) and the load (cam follower 744-6 and latch flag 744-5). While in this example, latch link 744-3 is implemented as a Class 1 lever, this is illustrative only and is not intended to be limiting. In other aspects, a Class 2 lever or a Class 3 lever could be used. For a Class 2 lever, the load is between the fulcrum and the effort, and for a Class 3 lever, the effort is between the fulcrum and the load.

A first end of spring 744-4 is connected to latch link 744-3 between first end 744-31 and the pivot point. A second end of spring 744-4 is connected to a third pin 704 extending from anchor bracket 541. Spring 744-4 provides a force on the first leg of latch link 744-3 that pulls cam follower 744-6 into latch socket 746-2.

For the configuration illustrated in FIG. 7A, cannula mount arm 355 is fully extended and latched in the extended position, as shown in FIGS. 4B and 5B. To arrive at this position, cam follower 744-6 moves up inclined ramp 746-1 (FIG. 7B) of latch 746 as cannula mount arm 355 is withdrawn.

The forces on the first leg of latch link 744-3 provided by springs 744-4 and 745-2 maintains cam follower 744-6 on inclined ramp 746-1. When cam follower 744-6 reaches the high end of inclined ramp 746-1 and cannula mount arm 355 is withdrawn further, springs 744-4 and 745-2 pull and hold cam follower 744-6 in socket 746-2 of latch 546. As cam follower 744-6 is pulled into socket 746-2, latch flag 744-5 is positioned in latch sensor 748. In this aspect, latch sensor 748 includes a pair of photo-interrupt switches so that if latch flag 744-5 is positioned in latch sensor 748, a light beam in each of the pair of photo-interrupt switches is broken. Breaking the light beams changes the state of the photo-interrupt switches, which is used to determine when cannula mount arm 355 is latched in the extended position. In this aspect, the pair of photo-interrupt switches is used for safety redundancy. If such redundancy is not needed, a single photo-interrupt switch could be used.

The use of a pair of photo-interrupt switches as a latch sensor is illustrative only and is not intended to be limiting. In other aspects, a capacitance switch or an inductive switch could be used. Alternatively, the latch mechanism could depress a switch that provides the cannula arm extended and locked signal.

When cannula mount arm 355 is locked in the extended position, to retract cannula mount arm 355 into curved distal end portion 391D, solenoid 545 is activated, sometime referred as being fired, either by depressing button 451 (FIG. 4B) or by the controller issuing a retract cannula mount arm command. When solenoid 545 is activated, solenoid 545 pulls plunger 745-1 linearly into the solenoid body, e.g., plunger 745-1 is moved proximally by activation of solenoid 545. The force from a linear solenoid is highly non-uniform, with the greatest force being applied at the fully retracted (most proximal) and the force dropping off rapidly as the plunger extends (in the distal direction). The geometry of links 744-1, 744-1, 744-2, and 744-3 is designed to compensate for this non-linearity of force, and to allow the solenoid to effectively lift cam follower 744-6 clear of latch 546.

The motion of plunger 745-1 causes second link 744-2 to exert a force in a first direction—downward—on second end 744-32 of latch link 744-3. The force in the first direction on second end 744-32 of latch link 744-3 causes latch link 744-3 to pivot about pin 703, which moves first end 744-31 of latch link 744-3 in a second direction, opposite to the first direction—upward—and extends spring 744-4. The motion of first end 744-31 of latch link 744-3 moves cam follower 744-6 out of socket 746-2 and above the highest point on inclined ramp 746-1. Similarly, latch flag 744-5 is moved out of latch sensor 748. Since cam follower 744-6 is no longer seated in latch 546, spring 543-3 automatically retracts cannula mount arm 355 into curved distal end portion 319D. The speed of the retraction is controlled by damper 648 as pinion gear 547 moves along gear teeth 642 on curved segment gear 542.

Figure 8:
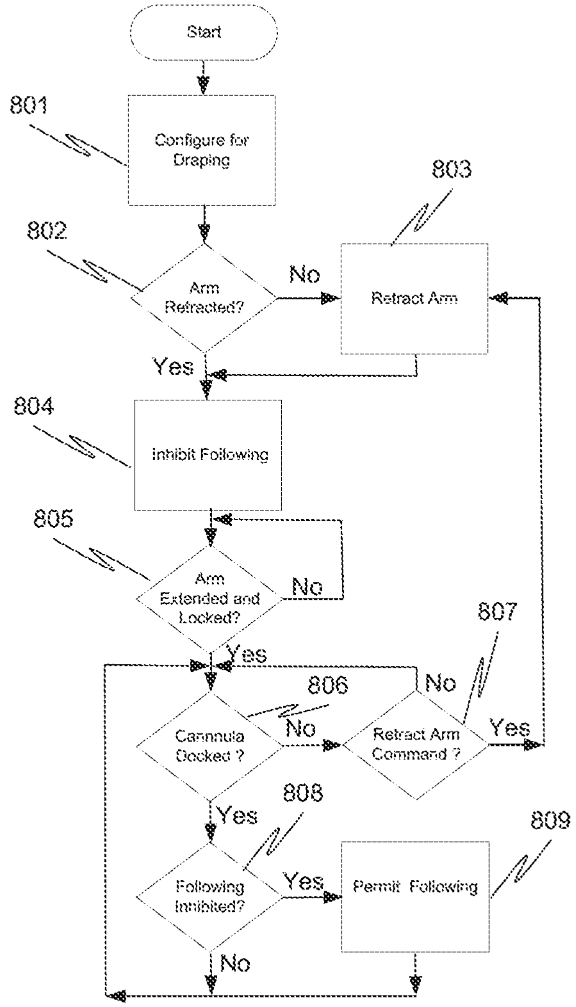
FIG. 8 is process flow diagram of acts used to control retraction of cannula mount arm in the telescoping cannula mount system.

FIG. 8 is process flow diagram of acts used to control retraction of cannula mount arm 355. The linear flow in FIG. 8 is used for ease of understanding only and is not intended to be limiting. The various processes in FIG. 8 might be performed in an order other than that illustrated by the linear flow, and could be perform simultaneously rather than sequentially.

Initially, a user accesses a user interface that includes a CONFIGURE FOR DRAPING 801 option. The user interface is generated by a controller in the computer-assisted surgical system that includes patient side support system 310. It should be appreciated that the controller can be made up of one unit, or multiple different units. When the controller is divided up among different units, the units may be centralized in one location or distributed across the computer assisted surgical system. Also, the different units of the controller may be given names that characterize the acts controlled by that unit of the controller.

When the user selects CONFIGURE FOR DRAPING 801 option, the controller configures patient side support system 310 to facilitate draping patient side support system 310. Here, only the acts related to controlling cannula mount arm 355 are considered in the configuring patient side support system 310 for draping.

In an ARM RETRACTED check process 802, the controller determines whether cannula mount arm 355 is parked within curved distal end portion 319D of link 319. If the signal from latch sensor 748 indicates cannula mount arm 355 is retracted in curved distal end portion 319D of link 319, ARM RETRACTED check process 802 transfers to an INHIBIT FOLLOWING process 804. Conversely, if the signal from latch sensor 748 indicates cannula mount arm 355 is not retracted in curved distal end portion 319D of link 319, ARM RETRACTED check process 802 transfers to a RETRACT ARM process 803. Note that a surgical system including patient side support system 310 typically has several features that are monitored to determine whether following is permitted or is inhibited. In FIG. 8, only the actions associated with cannula mount system 350 are considered with respect to the inhibiting and permitting of following.

In RETRACT ARM process 803, the controller first enables solenoid 545 and then activates solenoid 545. As described above, when activated, solenoid 545 causes locking assembly 544 to lift cam follower 744-6 out of latch 546, and consequently spring 543-3 automatically retracts cannula mount arm 355 into curved distal end portion 319D of link 319. RETRACT ARM process 803 transfers to INHIBIT FOLLOWING process 804. Thus, in this aspect, mechanical arm retraction system 540 is used to automatically change the shape of manipulator arm assembly 330 for draping.

When cannula mount arm 355 is parked in curved distal end portion 319D of link 319, cannula 470 is not docked on cannula mount arm 355. When cannula 470 is not docked, following is inhibited. Thus, in INHIBIT FOLLOWING process 804 following is inhibited based on a cannula not being docked. INHIBIT FOLLOWING process 804 transfers to ARM EXTENDED AND LOCKED check process 805.

ARM EXTENDED AND LOCKED check process 805 determines whether cannula mount arm 355 has been withdrawn from curved distal end portion 319D of link 319 and is locked in the extended position. If the signal from latch sensor 748 indicates cannula mount arm 355 is not latched in the extended position, ARM EXTENDED AND LOCKED check process 805 takes no action. Conversely, if the signal from latch sensor 748 indicates cannula mount arm 355 is latched in the extended position, ARM EXTENDED AND LOCKED check process 805 transfers to a CANNULA DOCKED check process 806. ARM EXTENDED AND LOCKED check process 805 should not be interpreted as requiring polling to determine whether cannula mount arm 355 is latched in the extended position. In one aspect, an event handler is used to detect an event that is fired when the signal from latch sensor 748 indicates cannula mount arm 355 is latched in the extended position.

Once cannula mount arm 355 is latched in the extended position, two events are of interest—a cannula is docked or a command to retract cannula mount arm 355 is issued. Thus, CANNULA DOCKED check process 806 determines whether a cannula has been mounted on extended cannula mount arm 355. If a signal is not received that a cannula is docked on cannula mount arm 355, CANNULA DOCKED check process 806 transfers to RETRACT ARM COMMAND check process 807. Conversely, if a signal is received that a cannula is docked on cannula mount arm 355, CANNULA DOCKED check process 806 transfers to FOLLOWING INHIBITED check process 808.

RETRACT ARM COMMAND check process 807 determines whether a command to retract cannula mount arm 355 into curved distal end portion 319D has been received. A command to retract cannula mount arm 355 can be generated by the user depressing arm retraction button 451 or by the controller issuing the command. As indicated above, cannula mount arm 355 can only be automatically retracted when a cannula is not docked on cannula mount arm 355. This condition is satisfied when processing transfers to RETRACT ARM COMMAND check process 807. Thus, if RETRACT ARM COMMAND check process 807 receives a command to retract cannula mount arm 355, RETRACT ARM COMMAND check process 807 transfers to RETRACT ARM process 803, and otherwise returns to CANNULA DOCKED check process 806.

The loop between RETRACT ARM process 803 and CANNULA DOCKED check process 806 should not be interpreted as requiring polling to determine whether a cannula was docked and whether a command to retract cannula mount arm 355 was received. In one aspect, an event handler is used to detect the appropriate conditions and to fire an appropriate event indicating the conditions detected.

After a cannula is first docked to cannula mount arm 355, the inhibition of following due to a cannula not being docked is removed, and then the next event of interest is undocking of the cannula. As described previously, cannula mount arm 355 cannot be retracted so long as cannula 470 is docked on arm 355.

Thus, FOLLOWING INHIBITED check process 808 determines whether following is inhibited because a cannula is not docked on cannula mount arm 355. If a cannula is docked on cannula mount arm 355, FOLLOWING INHIBITED check process 808 transfers to PERMIT FOLLOWING process 809, which removes the inhabitation of following by cannula mount system 350. If there is no cannula docked on cannula mount arm 355, FOLLOWING INHIBITED check process 808 returns to CANNULA DOCKED check process 806.

Note that even if cannula mount system 350 permits following, the controller may still inhibit following due to other conditions in the surgical system. PERMIT FOLLOWING process 809 considers only the state of cannula mount system 350 in determining whether to permit following and does not consider other factors that may be used to determine when the surgical system is actually permitted to enter following by the controller.

The loop between CANNULA DOCKED check process 806 and FOLLOWING INHIBITED check process 808 also should not be interpreted as requiring polling to determine whether a cannula was docked. In one aspect, an event handler is used to detect the appropriate conditions and to fire an appropriate event indicating the conditions detected.

Note that as long as a cannula is docked, a retract arm command is not acted upon, and so cannula mount arm 355 cannot be inadvertently retracted. During a surgical procedure, parts of one or more surgical instruments extend through cannula 470 into a patient. If cannula mount arm 355 were retracted while a cannula was docked, the inadvertent motion of the surgical instruments might harm the patient, and so the interlock on retraction is used to prevent retraction so long as a cannula is docked to arm 355.

Figure 9:
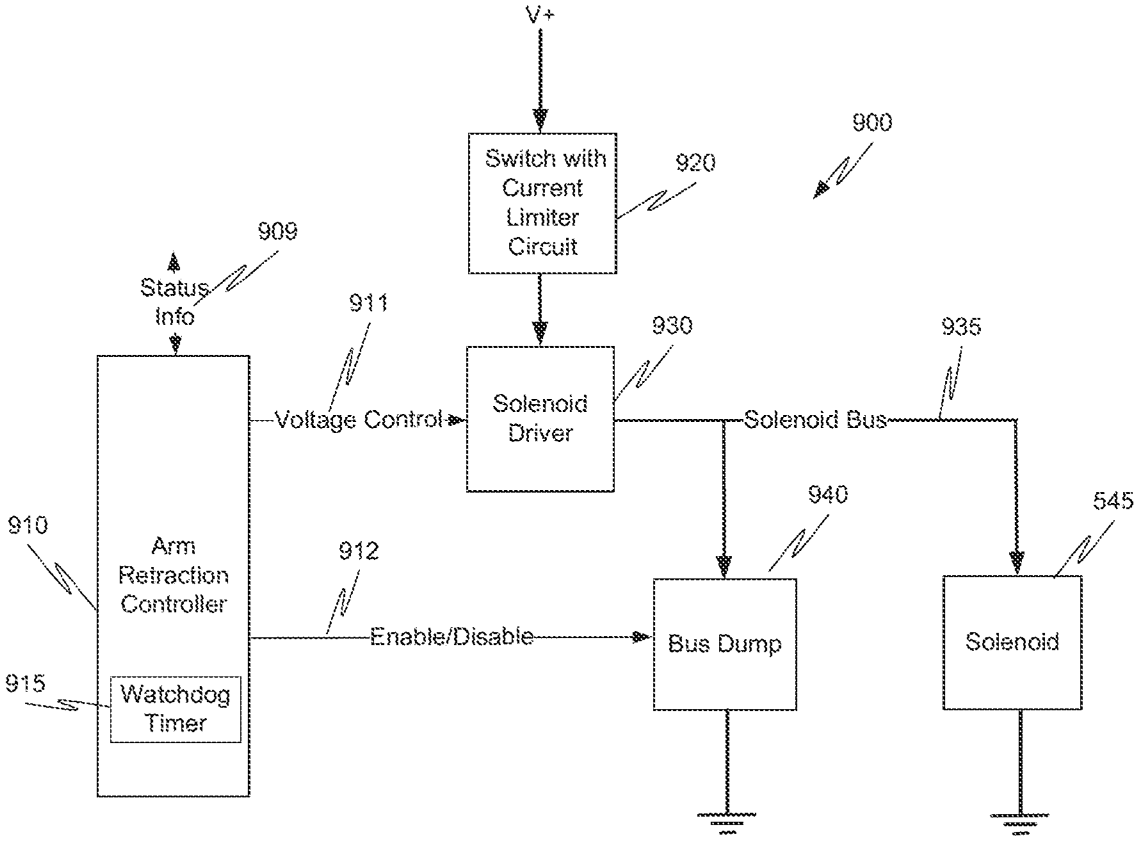
FIG. 9 is a block diagram of an interlock control system that implements an interlock that prevents retraction of the cannula mount arm when a cannula is mounted on the cannula mount arm.

FIG. 9 is a block diagram of an interlock control system 900 that implements an interlock that prevents retraction of cannula mount arm 355 when a cannula is mounted on cannula mount arm 355. An arm retraction controller 910, sometimes referred to as controller 910 receives system status information 909 that includes whether a cannula is docked on cannula mount arm 355. A voltage control line 911 is connected between arm retraction controller 910 and a solenoid driver 930. A switch with current limiter circuit 920 is positioned between a supply voltage V+ (48 volts in one aspect) and solenoid driver 930. Solenoid driver 930 is an example of an electric actuator driver. A solenoid bus 935 connects solenoid driver 930 to solenoid 545 and to a bus dump circuit 940. Solenoid bus 935 is an example of an electric actuator bus. Both solenoid 545 and bus dump circuit 940 are also connected to ground. An enable/disable line 912 connects arm retraction controller 910 to bus dump circuit 940.

When status information 909 indicates that a cannula is not mounted on cannula mount arm 355 and includes an arm retraction command, arm retraction controller 910 first generates a disable signal on enable/disable line 912 to bus dump circuit 940. The disable signal causes bus dump circuit 940 to open a connection, in bus dump circuit 940, between solenoid bus 935 and ground. Thus, when the disable signal is on enable/disable line 912, bus dump circuit 940 does not connect solenoid bus 935 to ground.

After the disable signal is activated on enable/disable line 912, arm retraction controller 910 provides a pulse width modulation duty cycle signal on voltage control line 911 to solenoid driver 930. The switch in switch with current limiter circuit 920 is normally closed and so supply voltage V+ is provided to solenoid driver 930. In response to the pulse width modulation duty cycle on voltage control line 911, solenoid driver 930 drives a series of pulses on solenoid bus 935, which activates solenoid 545. As described above, when solenoid 545 is activated, mechanical arm retraction system 540 is enabled and automatically retracts cannula mount arm 355.

After a brief time (less than the watchdog time, but long enough to unlatch cannula mount arm 355) controller 910 removes the pulse width modulation duty cycle signal on voltage control line 911 to solenoid driver 930. In response, solenoid driver 930 stops driving pulses on solenoid bus 935, which deactivates solenoid 545.

When a disable signal is generated on enable/disable line 912 by arm retraction controller 910, watchdog timer 915 is started. When watchdog timer 915 times out, the disable signal on enable/disable line to bus dump circuit 940 is changed to an enable signal. The enable signal causes bus dump circuit 940 to close a connection between solenoid bus 935 and ground in bus dump circuit 940. Thus, when the enable signal is on enable/disable line 912, bus dump circuit 940 connects solenoid bus 935 to ground.

Hence, bus dump circuit 940 operates as switch between solenoid bus 935 and ground, and the state of the switch—open or closed—is controlled by the signal on enable/disable line 912. Normally, bus dump circuit 940 is always shorting solenoid bus 935 to ground so that solenoid 545 cannot be fired. This only changes when both a cannula not mounted signal and an arm retraction command are present at the same time in status information 909.

As shown in FIG. 9, bus dump circuit 940 and solenoid 545 are connected in parallel between solenoid bus 935 and ground. The resistance in bus dump circuit 940 between solenoid bus 935 and ground is significantly lower than the resistance in solenoid 545 between solenoid bus 935 and ground. Thus, when bus dump circuit 940 is enabled, a large majority of the current flows from solenoid bus 935 through bus dump circuit 940 to ground. The remaining current that flows through solenoid 545 is insufficient to fire solenoid 545. Consequently, any voltage on solenoid bus 935 does not fire solenoid 545 when bus dump circuit 940 is enabled.

The logic in arm retraction controller 910 permits arm retraction controller 910 to generate a command on voltage control line 911 to fire solenoid 545 when both a cannula not mounted signal and an arm retraction command are present in status information 909, as just described. However, it is possible that arm retraction controller 910 generates a spurious command on voltage control line 911 to fire solenoid 545, or that there is a short between a power source—either in solenoid driver 930 or in the cabling—and solenoid bus 935. In each of these cases, bus dump circuit 940 is configured to connect solenoid bus 935 to ground, and so the spurious voltage does not fire solenoid 545.

If solenoid driver 930 unintentionally drives a voltage on solenoid bus 935 and thereby creates a large current through solenoid driver 930 and bus dump circuit 940, the current limiter circuit in switch with current limiter circuit 920 automatically opens the switch in circuit 920. Thus, when switch with current limiter circuit 920 detects an abnormal current draw, switch with current limiter circuit 920 disconnects the power to solenoid driver 930. This assures that the power supply, the circuitry in solenoid driver 930, and the circuitry in bus dump circuit 940 are not damaged by an excessive current draw.

If the switch in switch with current limiter circuit 920 fails open, solenoid 945 cannot be fired. This is a safe condition. If the switch in switch with current limiter circuit 920 fails closed, e.g., is shorted, this could defeat the safety system. Thus, each time the computer-assisted surgical system is powered on, the switch in switch with current limiter circuit 920 is tested to assure that the switch is not shorted.

If the switch in bus dump circuit 940 fails closed, e.g., shorted, this is a safe condition. If the switch in bus dump circuit 940 fails open, this could defeat the safety system. Thus, each time computer-assisted surgical system is powered on, the switch bus dump circuit 940 is tested to assure that the switch has not failed open.

In the event bus dump circuit 940 receives neither an enable command nor a disable command (possibly because of a broken connection on enable/disable line 912 or a failure in controller 910), bus dump circuit 940 automatically enables itself. This is another safeguard to insure that cannula mount arm 355 cannot be inadvertently retracted.

In one aspect, arm retraction controller 910 is implemented using a field programmable gate array circuit. In this aspect, bus dump circuit 940 is implemented using a metal-oxide-semiconductor field-effect transistor with the gate connected to enable/disable line 912.

Figure 10:
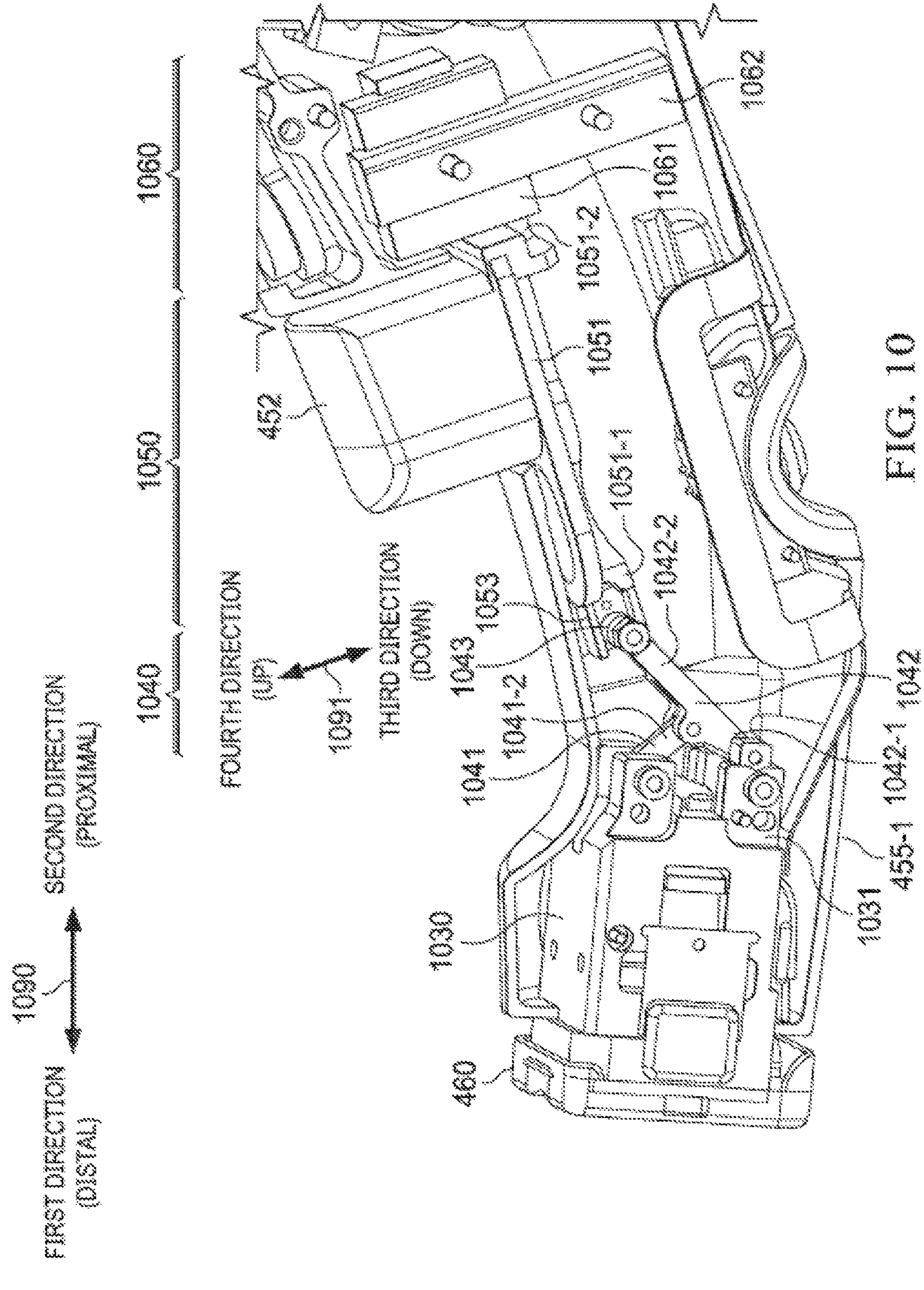
FIG. 10 is a cut away perspective view of the cannula mount arm to show a cannula mount assembly.

FIG. 10 is a cut away drawing of first end 455-1 of cannula mount arm 355 to show a cannula mount assembly. The cannula mount assembly includes a cannula docking assembly 1030, a linkage assembly 1040, a cannula release button assembly 1050, and a linear motion assembly 1060. This cannula mount assembly can be implemented in cannula mount arms other than those illustrated in the drawings.

Cannula docking assembly 1030 is coupled to a first end of cannula release button assembly 1050 by linkage assembly 1040. A second end of cannula release button assembly 1050 is coupled to linear motion assembly 1060. Linear motion assembly 1060 constrains cannula release button assembly 1050 to linear motion in third and fourth directions—down and up with respect to the outer surface of first end 455-1 of cannula mount arm 355—as represented by arrow 1091. The range of motion of cannula release button assembly 1050 along linear motion assembly 1060 in the third direction is limited by a portion of cannula release button assembly 1050 contacting a first hard stop within the housing of first end 455-1 of cannula mount arm 355.

When a force is applied on cannula release button 452, i.e., cannula release button 452 is depressed, cannula release button assembly 1050 moves linearly in the third direction—down in this example—along linear motion assembly 1060. Linkage assembly 1040 converts the linear motion of cannula release button assembly 1050 in the third direction to linear motion, in the second direction, e.g., in the proximal direction, of a moveable block 1154 (FIG. 11) within cannula docking assembly 1030, and in so doing compresses a spring 1160 in moveable block 1154. In one aspect, spring 1160 is implemented using two springs.

Here, the second direction—in this example, in the proximal direction—is a direction that is different from the fourth direction that is opposite the third direction, e.g., the up direction is different from the proximal direction. In FIG. 10 the third direction is a down direction and the fourth direction is an up direction as represented by arrow 1091. The first direction is a distal direction and the second direction is a proximal direction as represent by arrow 1090. Thus, as stated, the second direction is different from the fourth direction that is opposite to the third direction and is different from the third direction.

Similarly, when the downward force on cannula release button 452 is released, spring 1160 in cannula docking assembly 1030 moves moveable block 1154 linearly in the first direction—in the distal direction in this example—to a position where spring 1160 has a minimum potential energy. Linkage assembly 1040 coverts the linear motion of moveable block 1154 in the first direction to linear motion of cannula release button assembly 1050 in the fourth direction. Here, the first direction is in a direction that is different from the direction opposite the fourth direction. As pointed out above, the fourth direction is up in FIG. 10, and the direction opposite the fourth direction is the third direction (down), which is different from the first direction (distal direction). Cannula release button assembly 1050 is moved in the fourth direction by the force of spring 1160 and held in a location such that cannula release button 452 is in its undepressed position, as illustrated in FIGS. 10, 4B, and 5B.

Cannula release button assembly 1050 includes a frame 1051, cannula release button 452, and rail 1053. Frame 1051 includes a first end 1051-1 and a second end 1051-2. A linear slide 1061 of linear motion assembly 1060 is affixed to second end 1051-2 of frame 1051. Linear slide 1061 is constrained to slide along rail 1062 of linear motion assembly 1060. Rail 1053 is mounted in first end 1051-1 of frame 1051. Cannula release button 452 is mounted on frame 1051 adjacent linear slide 1061.

Linkage assembly 1040 includes a first link 1041, a second link 1042, and a cam follower 1043. A first end 1042-1 of second link 1042 is rotatably mounted on a pin extending from a housing 1031 of cannula docking assembly 1030. Thus, second link 1042 is grounded to housing 1031 of cannula docking assembly 1030. Cam follower 1043 is mounted on a second end 1042-2 of second link 1042. Cam follower 1043 rides within rail 1053 in first end 1051-1 of frame 1051 of cannula release button assembly 1050. Cam follower 1043 is constrained within rail 1053 so that cam follower 1043 can move in the first and second directions, but not in the third and fourth directions.

Figure 11:
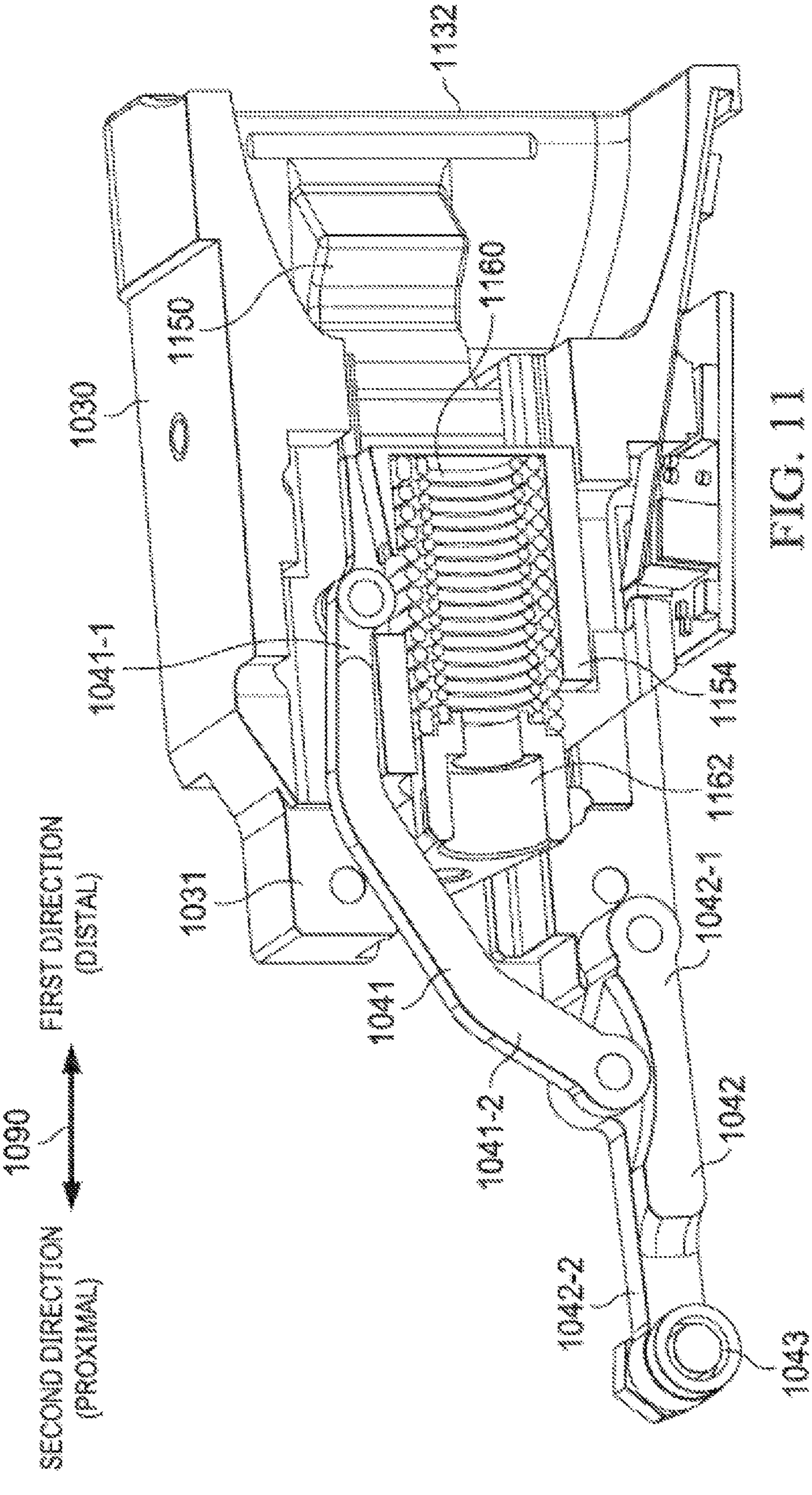
FIG. 11 is a cut away perspective view of the cannula docking assembly of FIG. 10.

A second end 1041-2 of first link 1041 is rotatably connected to a pin mounted in second link 1042. The pin is located between first end 1042-1 of second link 1042 and second end 1042-2 of second link 1042. A first end 1041-1 of first link 1041 is rotatably connected to a pin in moveable block 1154 (FIG. 11).

When cannula release button 452 is depressed, second link 1042 functions as a lever with a fulcrum provided by the pin extending from housing 1031. The effort is applied to second end 1042-2 and the load is located between the fulcrum and second end 1042-2. In this example, when cannula release button 452 is depressed, second link 1042 is a Class 2 lever because the load is between the fulcrum and the effort.

When cannula release button is released, second link 1042 still functions as a lever with a fulcrum provided by the pin extending from housing 1031. The load is at the second end 1042-2 and the effort is located between the fulcrum and second end 1042-2. In this example, when cannula release button 452 is released, second link 1042 is a Class 3 lever because the effort is between the fulcrum and the load. Thus, second link 1042 functions as both a Class 2 lever and a Class 3 lever. The class of lever is dependent on the direction that cannula release button 452 moves.

Thus, a force supplied by a user to depress cannula button 452 moves frame 1051, and consequently linear slide 1061 moves along rail 1062. As frame 1051 moves down, cam follower 1043 moves in the second direction. As second end 1042-2 of link 1042 moves in the second direction, link 1042 pivots about the pin in housing 1031. This motion moves first link 1041 in the second direction and in third direction. The motion of link 1041 moves moveable block 1154 in the second direction, which compresses spring 1160 in cannula docking assembly 1030, which releases a pair of clamping arms 1150 in cannula docking assembly 1030 so that pair of clamping arms 1150 can be opened.

When the force on cannula button 452 is released, spring 1160 expands and moves moveable block 1154 in the first direction, which closes the pair of clamping arms 1150. As moveable block 1154 moves in the first direction, first end 1041-1 of first link 1041 is moved in the first direction. The motion of first link 1041 in the first direction causes second link 1042 to pivot about the pin in housing 1031. Hence, second end 1042-2 of second link 1042 moves in the first direction and in the fourth direction as a result of moveable block 1154 moving in the first direction. The motion of second end 1042-2 of link 1042 is transferred to frame 1051 of assembly 1050, which linearly moves cannula release button 452 in the fourth direction until the motion of slide 1061 is stopped by a second hard stop within the housing of first end 455-1 of cannula mount arm 355.

The parts of cannula docking assembly 1030 needed to understand the operation of cannula release button 452 are shown in more detail in FIG. 11. Cannula docking assembly 1030 includes a pair of clamping arms 1150 to engage cannula 470. For example, when attachment portion 471 of cannula 450 is inserted into aperture 1132 of cannula docking assembly 1030, tips of clamping arms 1150 latch to depressions of cannula sterile adapter 460 that in turn are compressed by clamping arms 1150 into depressions 572 of attachment portion 471 to dock cannula 470 to cannula docking assembly 1030.

While it is not shown in FIGS. 10 and 11, each of clamping arms 1150 pivots about a pin to facilitate mounting and releasing cannula 470. Clamping arms 1150 are actuated by moveable block 1154 that engages and moves clamping arms 1150 into a closed (latched) position to dock cannula 470. For example, moveable block 1154 includes a cam surface that engages each of clamping arms 1150 to cause clamping arms 1150 to pivot to the closed position.

Spring 1160 biases moveable block 1154 to the position that closes each of clamping arms 1150. Spring 1160 is positioned between a mounting block 1162 and moveable block 1154.

Cannula docking assembly 1030 includes a sensor to detect the position of moveable block 1154 to infer whether clamping arms 1150 are in a locked or released position, as determined by the position of the cam surface on block 1154 relative to clamping arms 1150. The sensor, for example, may be a switch that moveable block 1154 contacts as moveable block 1154 is actuated back and forth to actuate clamping arms 1150. Output from the sensor is transmitted to the controller of the computer-assisted surgical system to provide feedback, for example, whether clamping arms 1150 are in a locked or released position. More details on a moveable block, clamping arms, and springs suitable for use in cannula docking assembly 1030 are presented in PCT International Publication No. WO2015/142814 A1, which was previously incorporated by reference.

Much of the previous discussion, including discussion associated with FIGS. 3, 4A-B, 5A-B, 6A-B, etc. refer to a patient side support system 310 with a manipulator arm assembly 330 having four links 313, 315, 317, 319 coupled by rotary joints. A telescoping cannula mount system 350 comprises a curved cannula mount arm 355 that can be extended from or parked within a curved distal end portion 319D of the fourth link 319.

Figure 12:
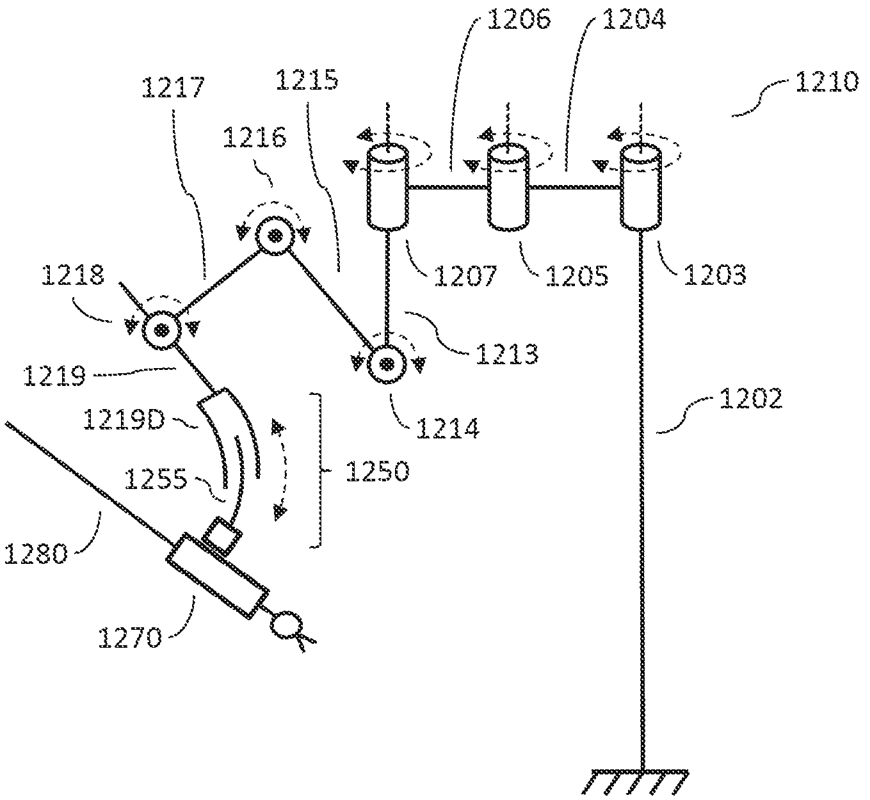
FIG. 12 is a schematic of a patient side support system with a telescoping cannula mount system.

Other designs of patient side support systems, manipulator arm assemblies, and shapes of telescoping cannula arm systems are contemplated and can be utilized in various embodiments. As some specific examples, FIG. 12 shows a schematic of a patient side support system 1210 that may be implemented with any appropriate number of links and active or passive joints (seven links 1202, 1204, 1206, 1213, 1215, 1217, 1219, six rotary joints 1203, 1205, 1207, 1214, 1216, 1218, and no prismatic joints are shown in FIG. 12). A telescoping cannula mount system 1250 comprises a cannula mount arm 1255 that can be extended from or parked within a distal end portion 1219D of the link 1219. A cannula 1270 can be mounted to the cannula mount arm 1255, and an instrument can be 1280 extended through the cannula 1270 to perform operations, as shown in FIG. 12.

Parts of patient side support system 1210 are analogous to corresponding parts in patient side support systems 110 and 310. For example, in various embodiments, links 1213, 1215, 1217, 1219 are analogous to links 113, 115, 117, 119 of patient side support systems 110 and links 313, 315, 317, 319 patient side support systems 310. Thus, the description associated with the earlier figures is not repeated here for FIG. 1*x*2.

Figure 13:
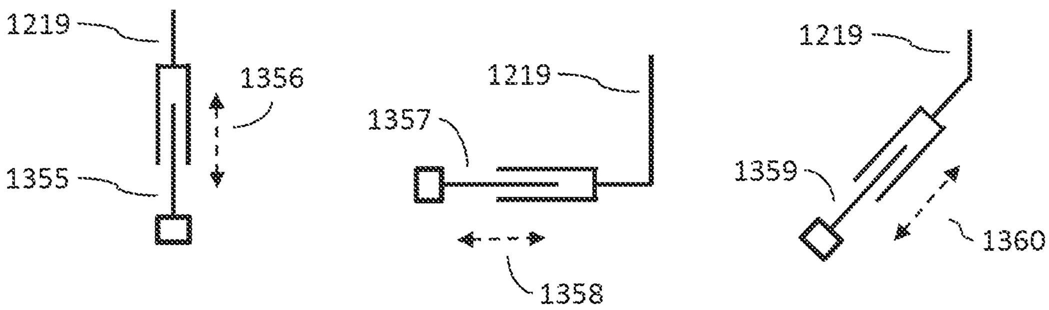
FIG. 13 show schematics of example telescoping cannula mount systems that can be used with the patient side support system of FIG. 12.

The cannula mount system 1250 is shown as curved in FIG. 12 for convenience, and can be any appropriate shape with any number of linear and nonlinear segments in various embodiments. FIG. 13 shows some example telescoping cannula mount systems with different linear shapes that can be used with the patient side support system of FIG. 12. Cannula mount arm 1355 extends and retracts along the main axis of the link 1219, as shown by the dotted-line arrow 1356. Cannula mount arm 1357 extends and retracts along an axis perpendicular to the main axis of 1219, as shown by the dotted-line arrow 1358. Cannula mount arm 1359 extends and retracts along an axis angled with respect to the main axis of link 1219, as shown by the dotted-line arrow 1360.

Although a controller is described above, it is to be appreciated that such a controller may be implemented in practice by any number of modules and each module may include any combination of components. Each module and each component may include hardware, software that is executed on a processor, and firmware, or any combination of the three. Also, the functions and acts of controller, as described herein, may be performed by one module, or divided up among different modules or even among different components of a module. When divided up among different modules or components, the modules or components may be centralized in one location or distributed across the computer-assisted surgical system for distributed processing purposes. Thus, references to the controller should not be interpreted as requiring a single physical entity as in some aspects the controller is distributed across the computer-assisted surgical system.

As used herein, "first," "second," "third," etc. are adjectives used to distinguish between different components or elements. Thus, "first," "second," and "third" are not intended to imply any ordering of the components or elements or to imply any total number of components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures were turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

Embodiments described above illustrate but do not limit the disclosure. It should also be understood that numerous modifications and variations are possible in accordance with the principles of the present disclosure. For example, in many aspects the devices described herein are used as single-port devices; i.e., all components necessary to complete a surgical procedure enter the body via a single entry port. In some aspects, however, multiple devices and ports may be used.

What is claimed is:

1. A system comprising:

a manipulator arm comprising a first link and a latch link coupled to the first link and configured to engage with a latch; and a cannula mount arm comprising the latch;

wherein:

the cannula mount arm is configured to be manually extended from the first link to an extended position, wherein extending the cannula mount arm stores potential energy in a spring;

the latch link is configured to engage with the latch when the cannula mount arm is extended from the first link to the extended position so as to lock the cannula mount arm in the extended position; and disengagement of the latch link from the latch results in the cannula mount arm being retracted into the first link using the potential energy stored in the spring.

2. The system of claim 1, wherein:

a first end of the spring is attached to the cannula mount arm; and a second end of the spring is coiled around a spool assembly.

3. The system of claim 2, wherein extending the cannula mount arm unwinds the spring from the spool assembly.

4. The system of claim 2, wherein:

the spool assembly is attached to a bracket; and the bracket is attached to a segment gear.

5. The system of claim 1, wherein the spring is a constant force spring.

6. The system of claim 1, wherein activation of an electrical component disengages the latch link from the latch.

7. The system of claim 6, wherein activation of the electrical component is inhibited when a cannula is docked to the cannula mount arm.

8. The system of claim 7, wherein power to the electrical component is shorted to ground when the cannula is docked to the cannula mount arm.

9. The system of claim 6, wherein the electrical component is a solenoid.

10. The system of claim 6, wherein:

the cannula mount arm further comprises an interlock control system;

the interlock control system comprises an actuator bus, a bus dump circuit, and the electrical component; and the bus dump circuit and the electrical component are connected between the actuator bus and a ground.

11. The system of claim 1, wherein:

the cannula mount arm is curved; and the first link is curved.

12. The system of claim 1, wherein the cannula mount arm further comprises a retraction button and a cannula release button.

13. The system of claim 1, wherein:

the cannula mount arm further comprises a cannula dock, a linkage assembly, a cannula release button having a first end and a second end, and a linear motion assembly;

the cannula dock is coupled to the first end of the cannula release button by the linkage assembly;

the second end of the cannula release button is coupled to the linear motion assembly; and the linear motion assembly is configured to constrain the cannula release button to linear motion in first and second directions.

14. The system of claim 1, further comprising a damper configured to limit a speed at which the cannula mount arm is retracted into the first link.

15. A cannula mount system comprising:

a cannula dock configured to receive a cannula;

a cannula mount arm; and a latch;

wherein:

the cannula mount arm is configured to be manually extended from a first link of a manipulator arm to an extended position, wherein extending the cannula mount arm stores potential energy in a spring;

the latch is configured to engage with a latch link of the manipulator arm when the cannula mount arm is extended from the first link to the extended position so as to lock the cannula mount arm in the extended position; and disengagement of the latch link from the latch results in the cannula mount arm being retracted into the first link using the potential energy stored in the spring.

16. The cannula mount system of claim 15, wherein:

a first end of the spring is attached to the cannula mount arm; and a second end of the spring is coiled around a spool assembly.

17. The cannula mount system of claim 16, wherein extending the cannula mount arm unwinds the spring from the spool assembly.

18. The cannula mount system of claim 15, wherein the spring is a constant force spring.

19. The cannula mount system of claim 15, wherein activation of an electrical component disengages the latch link from the latch.

20. The cannula mount system of claim 19, wherein activation of the electrical component is inhibited when a cannula is docked to the cannula mount arm.

* * * * *